(12) United States Patent
Hamprecht et al.

(10) Patent No.: US 7,737,275 B2
(45) Date of Patent: Jun. 15, 2010

(54) METHOD FOR PRODUCING 3-PHENYL(THIO)URACILS AND 3-PHENYLDITHIOURACILS

(75) Inventors: Gerhard Hamprecht, Weinheim (DE); Michael Puhl, Lampertheim (DE); Bernd Wolf, Fussgoenheim (DE); Michael Keil, Freinsheim (DE); Robert Reinhard, Ludwigshafen (DE); Werner Seitz, Plankstadt (DE); Guido Mayer, Goennheim (DE)

(73) Assignee: BASF Aktiengesellschaft, Luwigshafen (DE)

( * ) Notice: Subject to any disclaimer, the term of this patent is extended or adjusted under 35 U.S.C. 154(b) by 495 days.

(21) Appl. No.: 10/581,072

(22) PCT Filed: Dec. 1, 2004

(86) PCT No.: PCT/EP2004/013615

§ 371 (c)(1),
(2), (4) Date: May 31, 2006

(87) PCT Pub. No.: WO2005/054208

PCT Pub. Date: Jun. 16, 2005

(65) Prior Publication Data

US 2006/0293520 A1   Dec. 28, 2006

(30) Foreign Application Priority Data

Dec. 3, 2003   (DE) ................. 103 56 474

(51) Int. Cl.
*C07D 239/02* (2006.01)
*C07D 401/00* (2006.01)
*C07D 403/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)

(52) U.S. Cl. ..................... 544/309; 544/310
(58) Field of Classification Search ............ None
See application file for complete search history.

(56) References Cited

U.S. PATENT DOCUMENTS

| 4,309,209 | A |   | 1/1982 | Kobzina |  |
|---|---|---|---|---|---|
| 4,943,309 | A |   | 7/1990 | Bell |  |
| 5,169,430 | A | * | 12/1992 | Strunk et al. | 504/243 |
| 6,184,183 | B1 |   | 2/2001 | Andree et al. |  |
| 6,207,830 | B1 |   | 3/2001 | Sting |  |
| 2004/0235665 | A1 |   | 11/2004 | Zagar et al. |  |

FOREIGN PATENT DOCUMENTS

CA   2083071 A1   6/1993

(Continued)

OTHER PUBLICATIONS

Dorwald F. A. Side Reactions in Organic Synthesis, 2005, Wiley: VCH, Weinheim p. IX of Preface.*

(Continued)

*Primary Examiner*—James O Wilson
*Assistant Examiner*—Jeffrey H Murray
(74) *Attorney, Agent, or Firm*—Rothwell, Figg, Ernst & Manbeck, P.C.

(57) ABSTRACT

A process is described for preparing 3-phenyl(thio)uracils or 3-phenyldithiouracils of the formula I, by reacting a phenyl iso(thio)cyanate of the formula II with an enamine of the formula III and, if appropriate, in a further step, the resulting 3-phenyl(thio)uracil or 3-phenyldithiouracil of the formula I where $R^1=R^{1a}$, when $R^1$=hydrogen, is reacted with an aminating agent of the formula IV to give 3-phenyl(thio)uracils or 3-phenyldithiouracils of the formula I where $R^1$=amino

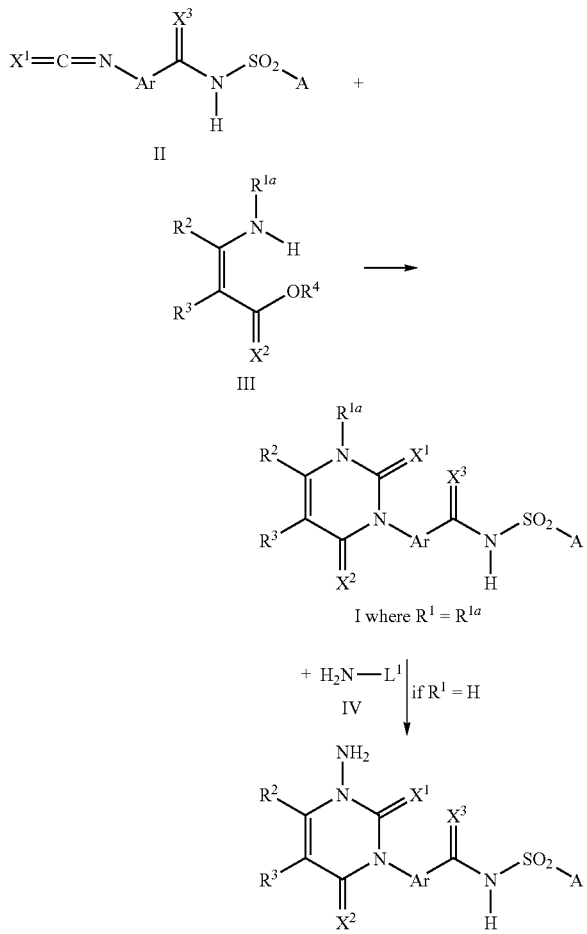

where the variables $R^1$, $R^{1a}$, $R^2$, $R^3$, $R^4$, $X^1$, $X^2$, $X^3$, Ar, A and L1 are each as defined in claim 1.

15 Claims, No Drawings

FOREIGN PATENT DOCUMENTS

| | | |
|---|---|---|
| CA | 2 485 360 A1 | 11/2003 |
| DE | 19741411 A1 | 3/1998 |
| EP | 0831091 A * | 3/1998 |
| WO | WO01/83459 * | 11/2001 |
| WO | WO 01/83459 A2 | 11/2001 |
| WO | WO03/240221 * | 3/2003 |
| WO | WO 03/097589 A1 | 11/2003 |

OTHER PUBLICATIONS

Kamal El-Dean et al., "Synthesis of Pyrimidines, Thienopyrimidines and Pyrazolopyrimidine", Journal of the Chinese Chemical Society, 2002, 49, 1057-1060.

Cervello et al., "An Improved Method for the Synthesis of Sulfonylureas", Synthesis, Mar. 1990, pp. 221-222.

Schwenkkraus et al., "Properties and Reactions of Substituted 1, 2-Thiazetidine 1, 1-Dioxides: Alkylation and Acylation of 3-Haloalkyl β-Sultams and Synthesis of Bicyclic β-SuRams", Arch. Pharm., 326, 437-441 (1993).

B.A. Arbuzov et al., "Bulletin of the Academy of Sciences of the USSR Division of Chemical Science", 39, 1990, 2610.

Sowada et al, "Über die Alkylierung 1,3-disubstituierter Schwefelsäurediamide", J. Prakt. Chem. 25, 1964, 88-94.

Unterhalt et al. "Trialkyl-und Tetraalkylsulfonyldiamide", Arch Pharm, 314,1981, 51-57.

Bancroft, "Synthesis and Reduction of Some 1,H-2,1,3-Benzothiadiazin-4(3H)one 2,2-Dioxides", J. Het. Chem., Dec. 15, 1978, 1521-1523.

Martinez et al., "Chlorophenylmethyl Benzothiadiazine Dioxides Derivatives: Potent Human Cytomegalovirus Inhibitors", Bioorganic & Medicinal Chemistry Letters, 9, (1999), 3133-3136.

* cited by examiner

METHOD FOR PRODUCING 3-PHENYL(THIO)URACILS AND 3-PHENYLDITHIOURACILS

CROSS REFERENCE TO RELATED APPLICATION

This application is a 35 USC §371 National Phase Entry Application from PCT/EP2004/013615 filed Dec. 1, 2004, and designating the United States.

SUMMARY OF THE INVENTION

The present invention relates to a process for preparing 3-phenyl(thio)uracils and 3-phenyldithiouracils of the formula I

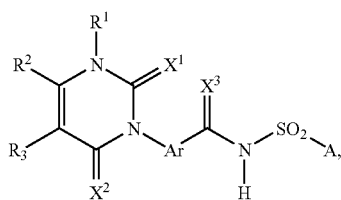

where the variables are each defined as follows:

$R^1$ is hydrogen, cyano, amino, $C_1$-$C_6$-alkyl, $C_1$-$C_3$-cyanoalkyl, $C_1$-$C_6$-haloalkyl, $C_1$-$C_6$-haloalkoxy, $C_3$-$C_7$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl;

$R^2$ and $R^3$ are each independently hydrogen, $C_1$-$C_6$-alkyl, $C_1$-$C_6$-haloalkyl, $C_3$-$C_7$-cycloalkyl, $C_2$-$C_6$-alkenyl, $C_2$-$C_6$-haloalkenyl, $C_3$-$C_6$-alkynyl or $C_3$-$C_6$-haloalkynyl;

$X^1$, $X^2$ and $X^3$ are each independently oxygen or sulfur;

Ar is phenyl, which may be mono- or polysubstituted by the following groups: hydrogen, halogen, cyano, $C_1$-$C_4$-alkyl or $C_1$-$C_4$-haloalkyl; and A is a radical derived from a primary or secondary amine or $NH_2$.

DESCRIPTION OF THE BACKGROUND ART

3-Phenyluracils of the formula I and the corresponding thio- and dithiouracils are known in principle from WO 01/83459. They are prepared in accordance with the teaching given in WO 01/83459 by the following processes A to C. In the following schemes A to C, the variables Ar and A are each as defined above, Hal is halogen and Q is an optionally substituted uracil, thiouracil or dithiouracil radical:

(A) condensation of a substituted benzoic acid with a substituted sulfuric diamide in the presence of N,N-carbonyldiimidazole (CDI) or conversion of the carboxylic acid to its acid chloride and subsequent reaction of the acid chloride with the sulfuric diamide in accordance with the following scheme A:

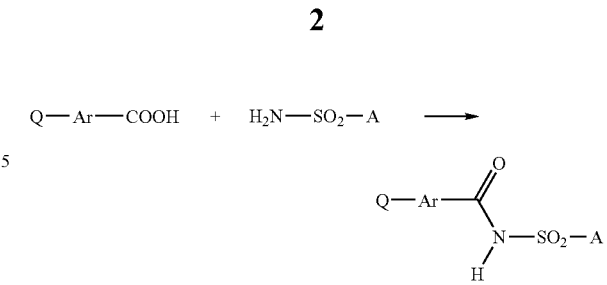

A disadvantage of this procedure is that the benzoic acid used is only obtainable from the precursor ester by cleavage using boron tribromide with corresponding salt formation. In addition, the yield of the condensation with sulfonic diamides is only between 16 and 45%. The detour via an acid chloride prepared beforehand also leads in only 26% yields to the desired benzoylsulfuric diamide, which additionally has to be freed of its impurities by chromatography.

(B) Replacement of a halogen atom by a uracil, thiouracil or dithiouracil radical by the following scheme B:

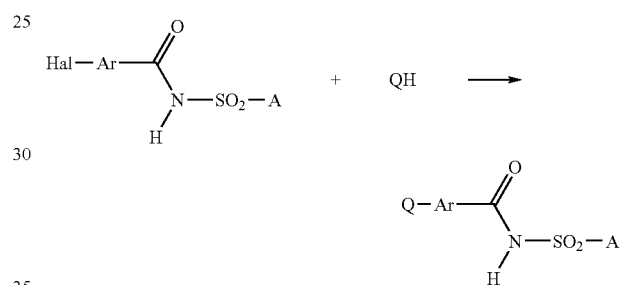

The process B has the disadvantage that the haloaromatic used first has to be prepared in a complicated manner by a Sandmeyer reaction. In addition, the selectivity of the reaction with respect to the halogen radical is unsatisfactory when further halogen substituents are present on Ar.

(C) Reaction of an aniline compound with an oxazinone and subsequent alkylation of the resulting 3-phenyluracil in the presence of a base according to the following scheme C:

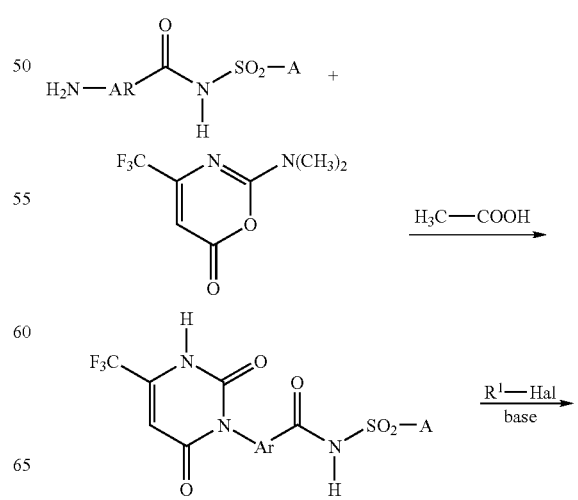

-continued

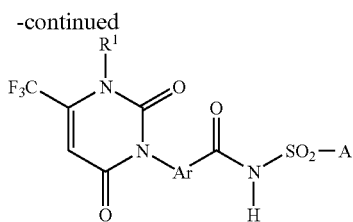

In this scheme, the variable $R^1$ is as defined above.

It is disadvantageous that the oxazinone used first has to be prepared in a costly and inconvenient manner by reacting an aminocrotonic ester with a dialkylcarbamoyl chloride and subsequently cyclizing with phosphorus oxychloride, phosphorus pentachloride or oxalyl chloride. This process is likewise not sufficiently economically viable as a consequence of the starting materials used and the reaction stages.

It is known that 3-phenyluracils can be prepared by reacting phenyl isocyanates with aminoalkenecarboxylic esters; see, for example, EP 0 831 091. However, the phenyl isocyanates used in EP 0 831 091 do not have an acylsulfonamide group.

Moreover, it is known that iso(thio)cyanate groups may enter into a multitude of different reactions with sulfonamide groups. For instance, iso(thio)cyanante groups may react with sulfonamide groups which bear a hydrogen atom on the nitrogen atom to form sulfonylureas. For example, J. Cervello and T. Sastre in Synthesis 1990, 221-222, describe the reaction of tolylsulfonamides with aryl isocyanantes to form the corresponding N-tosylurea.

U.S. Pat. No. 4,309,209 discloses that phenyl isocyanates react with chloromethane(N-methyl)-sulfonamide (=ClCH$_2$SO$_2$NHCH$_3$) to form a 1,2,4-thiadiazolidine-1,1,3-trione.

P. Schwenkkraus and H.-H. Otto in Arch. Pharm. (Weinheim) 326, 437-441 (1993) describe the reaction of 3-haloalkyl-β-sultams, i.e. cyclic sulfonamides, with phenyl isocyanate to form carbamoyl compounds.

DE 3433391 discloses the reaction of the cyclic sulfonamide saccharin with acyl isocyanates to give N-acylated saccharin derivatives.

B. A. Arbuzov, N. N. Zobova and N. R. Fedotava in JZV Akad Nauk SSSR, Ser Khim 1990, 2874 (engl. translation: Bulletin of the Academy of Sciences of the USSR, Division of Chemical Sciences, vol. 39, (1990) p. 2610) describe the N- and O-acylation of saccharin by reacting with a trifluoro-acetyl isocyanate.

SUMMARY OF THE INVENTION

It is an object of the present invention to provide a simple and economically viable process for preparing 3-phenyl(thio) uracils and -dithiouracils which allows high yields and high purity of product of value to be achieved.

We have found that this object is achieved by a process in which a phenyl iso(thio)cyanate of the formula II

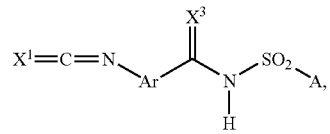

where the variables $X_1$, $X^3$, Ar and A are each as defined above is reacted with an enamine of the formula III

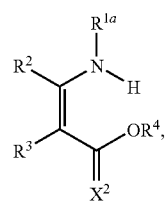

where
$R^{1a}$ is as defined above for $R^1$ with the exception of amino;
$R^2$, $R^3$ and $X^2$ are each as defined above; and
$R^4$ is $C_1$-$C_6$-alkyl, $C_1$-$C_6$-haloalkyl, $C_1$-$C_3$-alkoxy-$C_1$-$C_3$-alkyl, $C_1$-$C_3$-alkylthio-$C_1$-$C_3$-alkyl, $C_2$-$C_6$-alkenyl, $C_2$-$C_6$-haloalkenyl, $C_3$-$C_6$-alkynyl, $C_3$-$C_6$-haloalkynyl, $C_3$-$C_7$-cycloalkyl, $C_1$-$C_6$-cyanoalkyl or benzyl which is itself unsubstituted or substituted on the phenyl ring by methyl, methoxy, methylthio, halogen, nitro or cyano, preferably $C_1$-$C_6$-alkyl, $C_1$-$C_6$-haloalkyl, $C_2$-$C_6$-alkenyl, $C_2$-$C_6$-haloalkenyl, $C_3$-$C_6$-alkynyl, $C_3$-$C_6$-haloalkynyl or $C_1$-$C_3$-alkoxy-$C_1$-$C_3$-alkyl;

and, if appropriate, in a further step, the reaction of the resulting 3-phenyl(thio)uracil or 3-phenyldithiouracil of the formula I where $R^1$=$R^{1a}$, where $R^1$ is hydrogen, is reacted with an aminating agent of the formula IV $$H_2N\text{-}L^1 \qquad\qquad IV$$

where $L^1$ is a nucleophilic leaving group to give 3-phenyl (thio)uracils or 3-phenyldithiouracils of the formula I where $R^1$=amino.

DESCRIPTION OF EMBODIMENTS OF THE INVENTION

The present invention accordingly relates to a process for preparing 3-phenyl(thio)uracils or 3-phenyldithiouracils of the formula I where $R^1$=$R^{1a}$, which comprises the reaction of a phenyl iso(thio)cyanate of the formula II with an enamine of the formula III.

The present invention further provides a process for preparing the above-defined 3-phenyl(thio)uracils or 3-phenyldithiouracils of the formula I where $R^1$ is not hydrogen, in which the compounds I where $R^1$=hydrogen obtained by the process according to the invention are reacted with an aminating agent or alkylating agent.

The process according to the invention provides 3-phenyl (thio)uracils and -dithiouracils of the formula I in high yields and high purities. This is surprising in view of the fact that the substrate used has both an iso(thio)cyanate group and a sulfonamide group which can react together and would thus have been expected to result in a multitude of side reactions, including oligomer and polymer formation.

The organic molecular moieties specified in the definition of the substituents or as radicals on phenyl, naphthyl or heterocyclic rings constitute, like the definition halogen, collective terms for individual lists of the individual group members, the expression $C_n$-$C_m$ specifying the possible number of carbon atoms in the molecular moiety. All carbon chains, i.e. all alkyl, alkenyl and alkynyl moieties, may be straight-chain or branched. Unless stated otherwise, halogenated substituents preferably have from one to six identical or different halogen atoms. The definition halogen in each case represents fluorine, chlorine, bromine or iodine.

Examples of definitions include:

$C_1$-$C_4$-alkyl: for example methyl, ethyl, propyl, 1-methylethyl, butyl, 1-methyl-propyl, 2-methylpropyl or 1,1-dimethylethyl;

$C_1$-$C_{10}$-alkyl: a saturated aliphatic hydrocarbon radical having from 1 to 10 carbon atoms, e.g. $C_1$-$C_4$-alkyl, as specified above, and also, for example, n-pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, -4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl, 1-ethyl-3-methylpropyl, n-heptyl, n-nonyl, n-decyl, 1-methyl-hexyl, 1-ethylhexyl,-1-methylheptyl, 1-methyloctyl, 1-methylnonyl;

$C_2$-$C_{10}$-alkenyl: a monounsaturated olefinic hydrocarbon radical having from 2 to 10 carbon atoms, preferably from 3 to 6 carbon atoms, for example ethenyl, prop-2-en-1-yl (=allyl), prop-1-en-1-yl, but-1-en-4-yl, but-2-en-1-yl, but-3-en-1-yl, 1-methylprop-2-en-1-yl, 2-methylprop-2-en-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, 1-ethylprop-1-en-2-yl, n-hex-1-en-1-yl, n-hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, -4-methylpent-1-en-1-yl, 1-methylpent-2-en-1-yl, 2-methylpent-2-en-1-yl, 3-methylpent-2-en-1-yl, -4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4n-1-yl, 3-methylpent-4n-1-yl, -4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-2-en-1-yl, hept-2-en-1-yl, oct-2-en-1-yl, non-2-en-1-yl, dec-2-en-1-yl;

$C_2$-$C_{10}$-alkynyl: a hydrocarbon radical having from 2 to 10 carbon atoms, preferably from 3 to 6 carbon atoms, and a triple bond, for example, ethynyl, prop-2-yn-1-yl (=propargyl), prop-1-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, -4-methylpent-2-yn-4-yl, -4-methylpent-2-yn-5-yl, hept-2-yn-1-yl, oct-2-yn-1-yl, non-2-yn-1-yl, dec-2-yn-1-yl;

$C_1$-$C_4$-haloalkyl: a $C_1$-$C_4$-alkyl radical, as specified above, which is partly or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, -4-fluorobutyl, -4-chlorobutyl, -4-bromobutyl or nonafluorobutyl;

$C_1$-$C_{10}$-haloalkyl: $C_1$-$C_{10}$-alkyl as specified above where from 1 to 6 hydrogen atoms are substituted by halogen atoms, preferably by fluorine and/or chlorine, for example $C_1$-$C_4$-haloalkyl as specified above, and also 5-fluoropentyl, 5-chloropentyl, 5-bromopentyl, 5-iodopentyl, undecafluoropentyl, 6-fluorohexyl, 6-chlorohexyl, 6-bromohexyl or 6-iodohexyl;

$C_2$-$C_{10}$-haloalkenyl: $C_2$-$C_{10}$-alkenyl as specified above where from 1 to 6 hydrogen atoms are substituted by halogen atoms,-preferably by fluorine and/or chlorine, e.g. 2-chloroallyl, 3-chloroallyl, 2,3-dichloroallyl, 3,3-dichloroallyl, 2,3,3-trichloroallyl, 2,3-dichlorobut-2-en-1-yl, 2-bromoallyl, 3-bromoallyl, 2,3-dibromoallyl, 3,3-dibromoallyl, 2,3,3-tribromoallyl or 2,3-dibromobut-2-en-1-yl;

$C_2$-$C_{10}$-haloalkynyl: $C_2$-$C_{10}$-alkynyl as specified above where from 1 to 6 hydrogen atoms are substituted by halogen atoms, preferably by fluorine and/or chlorine, e.g. 1,1-difluoroprop-2-yn-1-yl, 1,1-difluorobut-2-yn-1-yl, 4-fluorobut-2-yn-1-yl, -4-chlorobut-2-yn-1-yl, 5-fluoropent-3-yn-1-yl or 6-fluorohex-4-yn-1-yl;

$C_1$-$C_{10}$-cyanoalkyl: $C_1$-$C_{10}$-alkyl substituted by a CN group, for example cyanomethyl, 1-cyanoethyl, 2-cyanoethyl, 1-cyanopropyl, 2-cyanopropyl, 3-cyanopropyl, 1-cyanoprop-2-yl, 2-cyanoprop-2-yl, 1-cyanobutyl, 2-cyanobutyl, 3-cyanobutyl, -4-cyanobutyl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl, 3-cyano-2,2-dimethylpropyl, 6-cyanohex-1-yl, 7-cyanohept-1-yl, 8-cyanooct-1-yl, 9-cyanonon-1-yl, 10-cyanodec-1-yl;

$C_3$-$C_{10}$-cycloalkyl: a cycloaliphatic radical having from 3 to 10 carbon atoms, for example, cyclopropyl, cyclobutyl, cyclopentyl, cyclohexyl, cycloheptyl, cyclooctyl, cyclononyl or cyclodecyl;

$C_3$-$C_{10}$-cycloalkenyl: a cycloaliphatic radical having from 3 to 10 carbon atoms and a double bond, for example cyclopropen-1-yl, cyclobuten-1-yl, cyclopenten-1-yl, cyclohexen-1-yl, cyclohepten-1-yl, cycloocten-1-yl, cyclononen-1-yl, cyclodecen-1-yl, cyclopent-2-en-1-yl, cyclohex-2-en-1-yl, cyclohept-2-en-1-yl, cyclooct-2- en-1-yl, cyclonon-2-en-1-yl, cyclodec-2-en-1-yl, cyclohex-3-en-1-yl, cyclohept-3-en-1-yl, cyclooct-3-en-1-yl, cyclooct-4-en-1-yl, cyclonon-3-en-1-yl, cyclonon-4-en-1-yl, cyclodec-4-en-1-yl or cyclodec-3-en-1-yl;

$C_1$-$C_4$-alkylcarbonyl: an alkyl radical having from 1 to 4 carbon atoms and bonded via a carbonyl group, for example acetyl, propionyl, butyryl or isobutyryl;

($C_1$-$C_4$-alkylamino)carbonyl: for example methylaminocarbonyl, ethylaminocarbonyl, propylaminocarbonyl, 1-methylethylaminocarbonyl, butylaminocarbonyl, methylpropylaminocarbonyl, 2-methylpropylaminocarbonyl or 1,1-dimethylethylaminocarbonyl;

di($C_1$-$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

$C_1$-$C_4$-alkoxy: an alkyl radical having from 1 to 4 carbon atoms and bonded via an oxygen atom, for example methoxy, ethoxy, propoxy, 1-methylethoxy, butoxy, 1-methylpropoxy, 2-methylpropoxy or 1,1-dimethylethoxy;

$C_1$-$C_4$-alkoxycarbonyl: an alkoxy radical having from 1 to 4 carbon atoms and bonded via a carbonyl group, for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

$C_1$-$C_4$-alkylthio ($C_1$-$C_4$-alkylsulfanyl: $C_1$-$C_4$-alkyl-S—): an alkyl radical having from 1 to 4 carbon atoms and bonded via a sulfur atom, for example methylthio, ethylthio, propylthio, 1-methylethylthio, butylthio, 1-methylpropylthio, 2-methylpropylthio or 1,1-dimethylethylthio;

$C_1$-$C_4$-alkylsulfinyl ($C_1$-$C_4$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl;

$C_1$-$C_4$-alkylsulfonyl ($C_1$-$C_4$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl;

phenyl-$C_1$-$C_4$-alkyl: e.g. benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, -4-phenylbut-1-yl, 1-phenylbut-2-yl, 2-phenylbut-2-yl, 3-phenylbut-2-yl, -4-phenylbut-2-yl, 1-(phenylmeth)eth-1-yl, 1-(phenylmethyl)-1-(methyl)eth-1-yl or -(phenylmethyl)-1-(methyl)prop-1-yl; preferably benzyl;

3- to 8-membered heterocyclyl: a heterocyclic radical which has 3, 4, 5, 6, 7 or 8 ring members where 1, 2 or 3 of the ring members are heteroatoms which are selected from oxygen, sulfur, nitrogen and an $NR^7$ group (where $R^7$ is hydrogen, $C_1$-$C_6$-alkyl, $C_3$-$C_6$-alkenyl or $C_3$-$C_6$-alkynyl). In addition, the heterocycle may if appropriate have one or two carbonyl groups or thiocarbonyl groups as ring members. The heterocycle may be aromatic (heteroaryl) or partly or fully saturated.

Examples of saturated heterocycles are:
oxiran-1-yl, aziridin-1-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-4-yl, 1,3-dithiepan-5-yl, 1,3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl;

Examples of unsaturated heterocycles are:
dihydrofuran-2-yl, 1,2-oxazolin-3-yl, 1,2-oxazolin-5-yl, 1,3-oxazolin-2-yl;

Examples of aromatic heterocyclyl are the 5- and 6-membered aromatic, heterocyclic radicals, e.g. furyl such as 2-furyl and 3-furyl, thienyl such as 2-thienyl and 3-thienyl, pyrrolyl such as 2-pyrrolyl and 3-pyrrolyl, isoxazolyl such as 3-isoxazolyl, 4-isoxazolyl and 5-isoxazolyl, isothiazolyl such as 3-isothiazolyl, 4-isothiazolyl and 5-isothiazolyl, pyrazolyl such as 3-pyrazolyl, 4-pyrazolyl and 5-pyrazolyl, oxazolyl such as 2-oxazolyl, 4-oxazolyl and 5-oxazolyl, thiazolyl such as 2-thiazolyl, 4-thiazolyl and 5-thiazolyl, imidazolyl such as 2-imidazolyl and 4-imidazolyl, oxadiazolyl such as 1,2,4-oxadiazol-3-yl, 1,2,4-oxadiazol-5-yl and 1,3,4-oxadiazol-2-yl, thiadiazolyl such as 1,2,4-thiadiazol-3-yl, 1,2,4-thiadiazol-5-yl and 1,3,4-thiadiazol-2-yl, triazolyl such as 1,2,4-triazol-1-yl, 1,2,4-triazol-3-yl and 1,2,4-triazol-4-yl, pyridinyl such as 2-pyridinyl, 3-pyridinyl and 4-pyridinyl, pyridazinyl such as 3-pyridazinyl and 4-pyridazinyl, pyrimidinyl such as 2-pyrimidinyl, 4-pyrimidinyl and 5-pyrimidinyl, and in addition 2-pyrazinyl, 1,3,5-triazin-2-yl and 1,2,4-triazin-3-yl, in particular pyridyl, furanyl and thienyl.

In a particularly preferred embodiment of the process according to the invention, the variables $R^1$, $R^2$ and $R^3$ are each defined as follows, in each case alone or in combination:

$R^1$ is hydrogen, amino or $C_1$-$C_4$-alkyl, in particular hydrogen, amino, methyl or ethyl;

$R^2$ is hydrogen, $C_1$-$C_4$-alkyl or $C_1$-$C_4$-haloalkyl, in particular hydrogen, methyl, difluoromethyl, difluorochloromethyl or trifluoromethyl;

$R^3$ is hydrogen.

In a further preferred embodiment of the process according to the invention, $X_1$, $X^2$ and $X^3$ are each oxygen.

The Ar group is preferably a group of the formula Ar-1

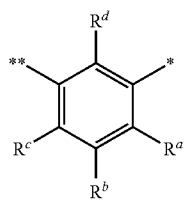

Ar-1 where $R^a$, $R^b$, $R^c$ and $R^d$ are each independently hydrogen, halogen, $C_1$-$C_4$-alkyl, $C_1$-$C_4$-haloalkyl or cyano;

\* indicates the bond of Ar to the $C(X^3)$ group; and

\*\* indicates the bond of Ar to the nitrogen atom of the (thio)uracil, dithiouracil radical or of the iso(thio)cyanato group.

In a particularly preferred inventive embodiment, the variables $R^a$, $R^b$, $R^c$ and $R^d$ are each defined as follows, in each case alone or in combination:

$R^a$ is halogen, cyano or $C_1$-$C_4$-haloalkyl, in particular fluorine, chlorine, cyano or trifluoromethyl;

$R^b$, $R^d$ are each hydrogen;

$R^c$ is hydrogen or halogen, in particular fluorine, chlorine or hydrogen.

The A radical which is derived from a primary or secondary amine is generally a group of the formula —$NR^5R^6$, where the variables $R^5$ and $R^6$ are each independently defined as follows:

$R^5$ and $R^6$ are each hydrogen, $C_1$-$C_{10}$-alkyl, $C_2$-$C_{10}$-alkenyl or $C_2$-$C_{10}$-alkynyl, each of which may be unsubstituted or substituted by one of the following radicals: $C_1$-$C_4$-alkoxy, $C_1$-$C_4$-alkylthio, CN, $NO_2$, formyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl, $C_1$-$C_4$-alkylsulfinyl, $C_1$-$C_4$-alkylsulfonyl, $C_3$-$C_{10}$-cycloalkyl, 3- to 8-membered heterocyclyl having from one to three heteroatoms selected from O, S, N and an $NR^7$ group where $R^7$ is hydrogen, $C_1$-$C_6$-alkyl, $C_3$-$C_6$-alkenyl or $C_3$-$C_6$-alkynyl, phenyl which may itself have 1, 2, 3 or 4 substituents selected from halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, $C_1$-$C_3$-alkylamino, $C_1$-$C_3$-dialkylamino, formyl, nitro or cyano;

$C_1$-$C_{10}$-haloalkyl, $C_2$-$C_{10}$-haloalkenyl, $C_2$-$C_{10}$-haloalkynyl, $C_3$-$C_8$-cycloalkyl, $C_3$-$C_{10}$-cycloalkenyl, 3- to 8-membered heterocyclyl having from one to three heteroatoms selected from O, S, N and an $NR^7$ group where $R^7$ is hydrogen, $C_1$-$C_6$-alkyl, $C_3$-$C_6$-alkenyl or $C_3$-$C_6$-alkynyl, phenyl or naphthyl, where $C_3$-$C_8$-cycloalkyl, $C_3$-$C_{10}$-cycloalkenyl, 3- to 8-membered heterocyclyl, phenyl or naphthyl, each of which may themselves have 1, 2, 3 or 4 substituents selected from halogen, $C_1$-$C_4$-alkyl, $C_1$-$C_4$-alkoxy, $C_1$-$C_4$-fluoroalkyl, $C_1$-$C_4$-alkyloxy-carbonyl, trifluoromethylsulfonyl, formyl, $C_1$-$C_3$-alkylamino, $C_1$-$C_3$-dialkylamino, phenoxy, nitro or cyano; or $R^5$ and $R^6$ together form a saturated or partially unsaturated 5- to 8-membered nitrogen heterocycle which may have, as ring members, one or two carbonyl groups, thiocarbonyl groups and/or one or two further heteroatoms selected from O, S, N and an $NR^7$ group where $R^7$ is hydrogen, $C_1$-$C_6$-alkyl, $C_3$-$C_6$-alkenyl or $C_3$-$C_6$-alkynyl, and which may be substituted by $C_1$-$C_4$-alkyl, $C_1$-$C_4$-alkoxy and/or $C_1$-$C_4$-haloalkyl.

Preferred substituents $R^5$ and $R^6$ are each independently hydrogen, $C_1$-$C_6$-alkyl which is optionally substituted by a substituent selected from halogen, cyano, $C_1$-$C_4$-alkoxy, $C_1$-$C_4$-alkoxycarbonyl, $C_1$-$C_4$-alkylthio, $C_3$-$C_8$-cycloalkyl, phenyl, which is itself optionally substituted by halogen or $C_1$-$C_4$-alkoxy, furyl, thienyl or 1,3-dioxolanyl.

Further preferred substituents $R^5$ and $R^6$ are $C_2$-$C_6$-alkenyl, $C_2$-$C_6$-alkynyl, $C_3$-$C_8$-cycloalkyl or phenyl which is optionally substituted by 1 or 2 substituents selected from halogen, $C_1$-$C_4$-alkyl, $C_1$-$C_4$-fluoroalkyl, $C_1$-$C_4$-alkoxy, $C_1$-$C_4$-alkoxycarbonyl, nitro or $C_1$-$C_3$-dialkylamino, naphthyl or pyridyl.

In a further preferred embodiment, $R^5$ and $R^6$ together form a five-, six- or seven-membered saturated or unsaturated nitrogen heterocycle which may comprise a further heteroatom-selected from N, O and an $NR^7$ group where $R^7$ is hydrogen, $C_1$-$C_6$-alkyl, $C_3$-$C_6$-alkenyl or $C_3$-$C_6$-alkynyl, as a ring member, and/or may be substituted by one, two or three substituents selected from $C_1$-$C_4$-alkyl and $C_1$-$C_4$-haloalkyl.

In a particularly preferred embodiment of the process according to the invention, one of the $R^5$ or $R^6$ radicals is hydrogen, $C_1$-$C_6$-alkyl, $C_2$-$C_6$-alkenyl or $C_2$-$C_6$-alkynyl and the other $R^5$ or $R^6$ radical is $C_1$-$C_6$-alkyl, $C_3$-$C_8$-cyclohexyl or phenyl.

Accordingly, the present invention relates in particular to a process for preparing 3-phenyl(thio)uracils or 3-phenyldithiouracils of the general formula I where Ar is Ar-1. These compounds are referred to hereinbelow as IA.

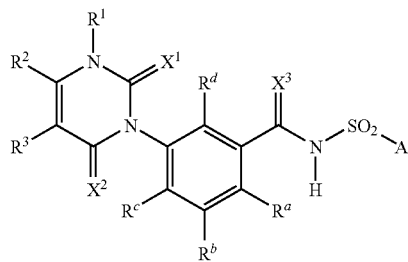

The variables $R^1, R^2, R^3, R^a, R^b, R^c, R^d, X^1, X^2, X^3$ and A are each as defined above.

The process comprises the conversion of a phenyl iso(thio)cyanate of the formula IIA

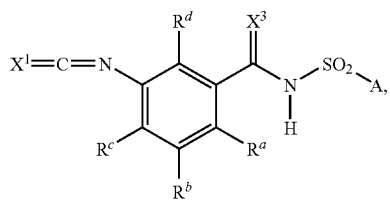

where
$X^1, X^3$ are each independently oxygen or sulfur;
$R^a, R^b, R^c$ and $R^d$ are each independently hydrogen, halogen, cyano, $C_1$-$C_4$-alkyl or $C_1$-$C_4$-haloalkyl; and
A is as defined above; and is in particular an $NR^5R^6$ group where $R^5$ and $R^6$ each have the above definitions, in particular the definitions specified as preferred or more preferred.

In particular the present invention relates to a process for preparing 3-phenyl(thio)uracils or 3-phenyldithiouracils IA where A is $NR^5R^6$; and
the variables $R^1, R^2, R^3, R^a, R^b, R^c, R^d, X^1, X^2$ and $X^3$ are each independently, but preferably in combination with each other, defined as follows:
$R^1$ is hydrogen, amino or $C_1$-$C_4$-alkyl, in particular hydrogen, amino, methyl or ethyl;
$R^2$ is hydrogen, $C_1$-$C_4$-alkyl or $C_1$-$C_4$-haloalkyl, in particular hydrogen, methyl, difluoromethyl, difluorochloromethyl or trifluoromethyl;
$R^3$ is hydrogen;
$R^a$ is halogen, cyano or $C_1$-$C_4$-haloalkyl, in particular fluorine, chlorine, cyano or trifluoromethyl;
$R^b, R^d$ are each hydrogen;
$R^c$ is hydrogen or halogen, in particular fluorine, chlorine or hydrogen;
$X^1, X^2$ and $X^3$ are each oxygen.

The process according to the invention comprises the reaction of a phenyl iso(thio)cyanate of the formula II with an enamine of the formula III to give 3-phenyl(thio)uracils or 3-phenyldithiouracils of the formula I where $R^1=R^{1a}$; and, if appropriate, in a further step, the reaction of the resulting 3-phenyl(thio)uracil or 3-phenyldithiouracil of the formula I where $R^1=R^{1a}$, when $R^1$ is hydrogen, with an aminating agent of the formula IV to give 3-phenyl(thio)uracils or 3-phenyldithiouracils of the formula I where $R^1$=amino:

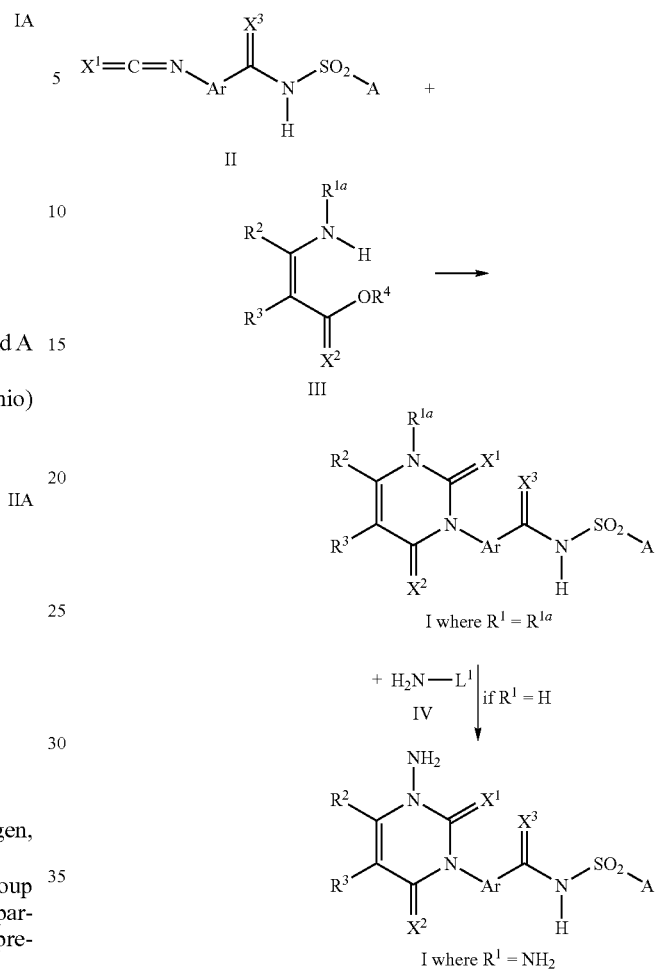

In general, the enamine III is reacted with the phenyl iso(thio)cyanate II in the presence of a base.

Useful bases are all customary organic and inorganic bases. Suitable inorganic bases comprise, for example, alkali metal and alkaline earth metal carbonates such as lithium carbonate, sodium carbonate, potassium carbonate, cesium carbonate, calcium carbonate, alkali metal and alkaline earth metal hydrides such as lithium hydride, sodium hydride, potassium hydride or calcium hydride.

Suitable organic bases comprise alkali metal and alkaline earth metal alkoxides such as lithium methoxide, sodium methoxide, potassium methoxide, calcium methoxide, lithium ethoxide, sodium ethoxide, potassium ethoxide, calcium ethoxide, sodium n-propoxide or isopropoxide, potassium n-propoxide or isopropoxide, sodium n-butoxide, isobutoxide, sec-butoxide or tert-butoxide, potassium n-butoxide, isobutoxide, sec-butoxide or tert-butoxide, sodium n-pentoxide, isopentoxide, sec-pentoxide or tert-pentoxide, potassium n-pentoxide, isopentoxide, sec-pentoxide or tert-pentoxide (=tert-amylate), tertiary amines such as tributylamine, pyridine, 1,8-diazabicyclo[5.4.0]undec-7-ene (DBU), 1,5-diazabicyclo[4.3.0]non-5-ene (DBN) or 1,4-diazabicyclo[2.2.2]octane (DABCO).

Suitable bases are also organolithium compounds such as n-butyllithium, sec-butyl-lithium, phenyllithium and alkali metal amides such as lithium diisopropylamide and sodium (bis(trimethylsilyl))amide. Also suitable are cesium fluoride and also alkali metal and alkaline earth metal hydroxides such as sodium hydroxide, potassium hydroxide, lithium hydroxide, calcium hydroxide. Preferred bases are alkali metal alkoxides, in particular lithium, sodium and potassium alkoxides of the abovementioned $C_1$-$C_5$-alkanols, the aforementioned alkali metal hydrides, alkali metal carbonates and amidine bases. In a particularly preferred embodiment of the process according to the invention, the base used is sodium hydride or potassium methoxide.

In general, from 0.9 to 6, preferably from 0.9 to 3, in particular from 1.0 to 3 and most preferably from 1.8 to 2.6, base equivalents are used per mole of the phenyl iso(thio)cyanate of the formula II.

The enamine of the formula III may be used in a substoichiometric, equimolar or superstoichiometric amount, based on the phenyl iso(thio)cyanate of the formula II. In general, from 0.9 to 1.3 mol, preferably from 0.95 to 1.15 mol, of enamine of the formula III are used per mole of the phenyl iso(thio)cyanate of the formula II.

A phenyl iso(thio)cyanate of the formula II is typically reacted with the enamine of the formula III in a solvent or diluent. For this purpose, useful solvents are all inert, organic solvents or solvent mixtures. For these reactions, the solvents used are, depending on the temperature range, aliphatic, cycloaliphatic or aromatic hydrocarbons such as pentane, hexane, cyclopentane, cyclohexane, toluene, xylene, chlorinated hydrocarbons such as dichloromethane, trichloromethane, 1,2-dichloroethane, 1,1,2,2-tetrachloroethane, chlorobenzene, 1,2-, 1,3- or 1,4-dichlorobenzene, ethers such as tetrahydrofuran, 1,4-dioxane, anisole, glycol ethers such as dimethyl glycol ether, diethyl glycol ether, diethylene glycol dimethyl ether, esters such as methyl acetate, ethyl acetate, propyl acetate, n-butyl acetate, methyl isobutyrate, isobutyl acetate, carbonates such as dimethyl carbonate, diethyl carbonate and ethylene carbonate, carboxamides such as N,N-dimethylformamide, N,N-dimethylacetamide, N-methylpyrrolidone, nitrohydrocarbons such as nitrobenzene, tetraalkylureas such as tetraethylurea, tetrabutylurea, dimethylethyleneurea, dimethylpropyleneurea, nitriles such as acetonitrile, propionitrile, butyronitrile or isobutyronitrile, sulfoxides such as dimethyl sulfoxide or else mixtures of the solvents mentioned.

As long as the base has solvent properties, as in the case of pyridine and of tributylamine, the base or a mixture of the base with one of the aforementioned solvents may also be used as the solvent or diluent for the reaction of II with III.

Particular preference is given to an aprotic polar solvent system which also comprises mixtures of different aprotic polar solvents and mixtures of different aprotic polar solvents with aprotic nonpolar solvents. The proportion of polar aprotic solvent in such solvent systems is at least 50% by volume, preferably at least 75% by volume, in particular at least 85% by volume. Preferred aprotic polar solvents are the said N,N-dimethylamides of aliphatic $C_1$-$C_4$-carboxylic acids such as N,N-dimethylformamide and N,N-dimethylacetamide, N-methyllactams such as N-methylpyrrolidone, carbonates such as dimethyl carbonate, diethyl carbonate and ethylene carbonate, nitriles such as acetonitrile, propionitrile, butyronitrile and isobutyronitrile, sulfoxides such as dimethyl sulfoxide, cyclic ethers such as tetrahydrofuran and dioxane, esters such as ethyl acetate, n-butyl acetate or mixtures thereof and preferably among these the dimethylcarboxamides.

In a preferred embodiment, at least one aprotic polar solvent is used as the sole solvent system (more than 99% by volume based on the total volume), for example a mixture of N,N-dimethylformamide and tetrahydrofuran. In a further preferred embodiment of the invention, a solvent system is used which, in addition to the aprotic polar solvent, in particular in addition to the particularly preferred aprotic polar solvent, comprises from 0.5 to 25% by volume of at least one aprotic nonpolar solvent, in particular at least one aromatic or aliphatic hydrocarbon, especially toluene or hexane. Accordingly, the proportion of aprotic polar solvent in this mixture is from 75.0 to 99.5% by volume. Preferred aprotic nonpolar solvents are aliphatic hydrocarbons such as n-hexane, isohexane (commercial hexane mixture), n-heptane, decane, petroleum ether, cycloaliphatic hydrocarbons such as cyclohexane and aromatic hydrocarbons such as toluene, benzene or xylene.

Investigations have shown that the yield of product of value I is impaired by the presence of traces of water in the reaction mixture. In a preferred embodiment of the process according to the invention, the materials used are dried to such an extent that the content of water in the aprotic polar solvent is not more than 0.5% by weight, frequently not more than 0.2% by weight, preferably not more than 0.05% by weight, and in particular not more than 0.02% by weight, of water, based on the total amount of reactant II, reactant III and solvent. The quantitative determination of water may be effected chemically, for example by Karl-Fischer titration, or physically, for example by determining the dielectric constant, or quantitative HPLC.

In a preferred embodiment, the process according to the invention therefore also comprises a pretreatment of the solvent or diluent and/or of the reactants to dry the chemicals used. Processes for drying solvents are known to those skilled in the art in the field of organic synthesis, for example by using drying agents.

A preferred process comprises the drying by azeotropic drying. In azeotropic drying, the substance to be dried is admixed with a chemical which forms an azeotrope with water (azeotroping agent) and the aqueous azeotrope is subsequently removed by distillative means. Typically, the azeotroping agent is an organic solvent. Examples thereof are hydrocarbons such as benzene, toluene, xylene, pentane or hexane, chloroaromatics such as chlorobenzene and alkyl esters of aliphatic carboxylic acids such as ethyl acetate and n-butyl acetate.

In a preferred embodiment, the enamine III is initially charged in the aprotic polar solvent or diluent, for example N,N-dimethylformamide. Subsequently, from 20 to 200% by volume, preferably from 50 to 150% by volume and in particular from 80 to 130% by volume, based on the aprotic polar solvent or diluent, of an azeotroping agent suitable for this purpose is added and the mixture is dried azeotropically. The drying time required naturally depends upon the water content of the substances used, upon the batch size and upon the apparatus used and may be determined by routine methods by those skilled in the art. Finally, the enamine III is reacted with the phenyl iso(thio)cyanate II in the manner described hereinbelow.

In the process according to the invention, the reactants and reagents may in principle be combined in any order, i.e. the reactants and the base may be introduced into the reaction vessel and reacted separately simultaneously or in succession. In all process variants, preference is given to reacting the enamine III, the base and/or the phenyl iso(thio)cyanate II diluted in one of the aforementioned solvents or solvent mixtures.

Advantageously, the enamine III is initially charged and the base is added to the reaction mixture with mixing, for example stirring. The reaction temperature when the base is added depends upon the reactivity of the base used. In general, it is in the range from −20° C. to 80° C. Advantageously, stirring is continued at the same temperature or higher temperature to complete the reaction. The reaction times required may be determined by those skilled in the art with the aid of routine methods.

Advantageously, the base is added to the enamine III. In general, the addition of the base is effected under temperature control. For example, the alkali metal or alkaline earth metal hydrides are added to the enamine III, preferably within a temperature range of from −20° C. to 20° C., and stirred within this temperature range to complete the deprotonation of the enamine. When alkali metal or alkaline earth metal carbonates are used, the base is added to the enamine III generally at temperatures of not more than 50° C., in particular not more than 45° C., for example in the range from 20° C. to 50° C., and stirring is continued at temperatures of up to 80° C., for example from 35 to 80° C. When alkali metal and alkaline earth metal alkoxides are used, the base is added especially at temperatures of from −20° C. to 50° C., advantageously from −15° C. to 20° C., and stirring is continued at temperatures of from −10° C. to 80° C. Afterward, the phenyl iso(thio)cyanate II is added and the reaction is conducted to completion.

In the case that alkali metal or alkaline earth metal alkoxides or carbonates are used, it will be appreciated that the base may also be initially charged in a dried, polar solvent, then the enamine III added in one of the aforementioned dried, polar solvents or solvent mixtures, or may be dried azeotropically as described above and then the phenyl iso(thio)cyanate II added. Alternatively, the compounds II and III may also be initially charged as a mixture in one of the aforementioned dried, polar solvents or solvent mixtures and the base subsequently added in one of the aforementioned dried solvents or solvent mixtures. In one further variant of the process according to the invention, the base is initially charged in the aforementioned dried solvent or solvent mixtures and then a mixture of compound II and III is added in one of the aforementioned dried solvents or solvent mixtures.

Preference is given to carrying out the reaction in such a way that the base is added to the enamine of the formula III in one of the aforementioned dried solvents or solvent mixtures. After the continued stirring, the phenyl iso(thio)cyanate II is added in one of the aforementioned solvents or solvent mixtures and reaction is allowed to continue.

The reaction temperature for the reaction of the phenyl iso(thio)cyanate II with the enamine III in the presence of a base is generally in the range from −20 to 80° C.

When alkali metal or alkaline earth metal hydrides are used as a base, the phenyl iso(thio)cyanate II is generally added at a temperature of from −20° C. to 20° C., preferably from −5 to 10° C., to the mixture of base and enamine II, and stirring is then continued at temperatures up to 50° C., for example from 20 to 50° C.

When alkali metal and alkaline earth metal alkoxides are used, the phenyl iso(thio)-cyanate II is typically added at a temperature of from −20° C. to 20° C., preferably from −15° C. to 10° C., to the mixture of base and enamine III, and stirring is continued at temperatures up to 80° C., for example from 0 to 80° C.

When alkali metal and alkaline earth metal carbonates are used, the phenyl iso(thio)cyanate II is typically added to the mixture of base and enamine III at temperatures up to 50° C., for example from 20 to 50° C., and, to complete the reaction, stirring is subsequently continued at temperatures up to 80° C., for example from 20 to 80° C., preferably from 40 to 80° C. The reaction time required to achieve the desired conversion may be determined by routine methods by those skilled in the art.

The reaction may be carried out at atmospheric pressure, and also at reduced pressure or under elevated pressure, continuously or batchwise. In general, it is advantageous to carry out the reaction under a protective gas atmosphere such as nitrogen.

The workup to recover the target product may be effected by the processes customary for this purpose. To this end, the basic reaction mixture will generally be adjusted to a pH of ≦4, in particular ≦2, by adding acid, and crystallization or precipitation of the compound I will subsequently be brought about by adding water. Addition of acid and water may also be effected simultaneously, for example by adding a dilute aqueous acid. In principle, the reaction mixture may also be worked up by aqueous extraction, for example by, after neutralizing the alkaline reaction mixture, partitioning it, if appropriate after removing the majority of the solvent, between water and a water-immiscible organic solvent and subsequently isolating the compound I from the organic phase. These methods may be followed by further steps for purification, for example precipitation, crystallization and/or extractive steps.

The enamines of the formula III required as reactants to carry out the process according to the invention are known compounds and/or can be prepared in a similar manner to known processes (for example A. Lutz and S. Troto, J. of Heterocyclic Chem. 1972, 9, 3, 513-522).

The phenyl iso(thio)cyanates of the formula II and processes for their preparation are the subject matter of the prior German patent application 102 50 614.0, whose disclosure content is incorporated by way of reference. This process comprises the reaction of a compound VI

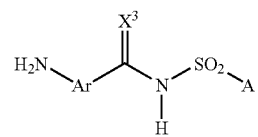

where $X^3$, Ar and A are each as defined above with a phosgenating agent such as phosgene, thiophosgene or diphosgene, in high yield and purity.

Compound VI is typically reacted with the phosgenating agent in an inert organic solvent. Useful solvents for these reactions, depending upon the temperature range, are hydrocarbons such as pentane, hexane, cyclopentane, cyclohexane, toluene, xylene, chlorinated hydrocarbons such as methylene chloride, chloroform, 1,2-dichloroethane, 1,1,2,2-tetrachloroethane, chlorobenzene, 1,2-, 1,3- or 1,4-dichlorobenzene, ethers such as 1,4-dioxane, anisole, glycol ethers such as dimethyl glycol ether, diethyl glycol ether, diethylene glycol dimethyl ether, esters such as ethyl acetate, propyl acetate, n-butyl acetate, methyl isobutyrate, isobutyl acetate, carboxamides such as N,N-dimethylformamide, N-methylpyrrolidone, carbonates such as dimethyl carbonate, diethyl carbonate, ethylene carbonate, nitrohydrocarbons such as nitrobenzene, tetraalkylureas such as tetraethylurea, tetrabutylurea, dimethylethyleneurea, dimethylpropyleneurea, nitrites such as acetonitrile, propionitrile, butyronitrile or isobutyronitrile, or else mixtures of individual solvents.

When phosgene is used, preference is given to using a solvent which has been substantially freed of protic impurities such as water and alcohols. However, when isothiocyanates are prepared, it is also possible, based on Houben-Weyl, Methoden der organischen Chemie [Methods of Organic Chemistry], 4th edition, vol. IX, p. 875, to carry out the reaction of II with thiophosgene in a biphasic system composed of water and a water-immiscible organic solvent or else in water.

The reaction temperature will generally not exceed 180° C., preferably 120° C. and especially 100° C., and will generally be at least 40° C. and preferably at least 50° C. Frequently, the procedure will be to add at least the majority of the phosgenating agent at a low temperature, for example in the range from 0 to 40° C., in particular from 10 to 40° C. and especially from 20 to 30° C., and, during or on completion of addition, to heat to a temperature in the range from 40 to 180° C., in particular from 50 to 120° C. and especially from 70 to 100° C., until the conversion is complete.

In general, from 0.9 to 2, preferably from 0.95 to 1.5, more preferably from 0.98 to 1.09, molar equivalents of phosgenating agent are used per mole of the compound VI.

If appropriate, the conversion of VI is carried out in the presence of a base. Useful bases are, for example, basic inorganic compounds, for example alkali metal or alkaline earth metal hydroxides, hydrogencarbonates or carbonates. However, the reaction may also be carried out in the presence of an organic base, for example of a tertiary amine such as triethylamine, tri-n-propylamine, N-ethyidiisopropylamine, tri-n-butylamine, pyridine, α-, β-, γ-picoline, 2,4-, 2,6-lutidine, N-methylpyrrolidine, dimethylaniline, N,N-dimethylcyclohexylamine, quinoline or acridine. The base (calculated as the base equivalent) may be used in a substoichiometric, superstoichiometric or equimolar amount, based on the compound VI. Per mole of the compound VI, generally from 0.01 to 6 mol, preferably from 0.1 to 3 mol, of base are used.

In another embodiment of the process, the reaction is carried out in the presence of hydrogen chloride. The amount of hydrogen chloride is then typically from 0.9 to 5.0 mol, preferably from 1.0 to 2.5 mol and in particular from 1.0 to 1.2 mol, of hydrogen chloride per mole of the compound VI. The procedure will generally be to initially introduce the aforementioned amount of gaseous hydrogen chloride into a solution or suspension the compound VI in one of the aforementioned solvents, or to add a solution of hydrogen chloride in a solvent, then to add the phosgenating agent in the manner described above and then to continue the reaction in the manner described above. Hydrogen chloride is typically introduced at temperatures between 10° C. and 60° C., preferably from 20 to 30° C.

When the process is carried out in the presence of hydrogen chloride, activated carbon may be used as the catalyst. Appropriately, the amount of activated carbon is from 1 to 10% by weight, preferably from 1 to 3% by weight, based on the weight of the compound VI.

The compounds of the general formula VI are likewise disclosed by the prior German patent application DE 102 50 614.0. The compounds of the formula VI may be obtained in a similar manner to known processes for preparing anilines.

The aniline compounds of the formula VI may be prepared, for example, according to scheme 1, by initially reacting an aroyl compound of the formula VII with a sulfuric diamide VIII in a condensation reaction to give an N-aroylsulfuric diamide of the general formula IX and subsequently reducing the resulting N-aroylsulfuric diamide IX to give the compound VI.

Scheme 1:

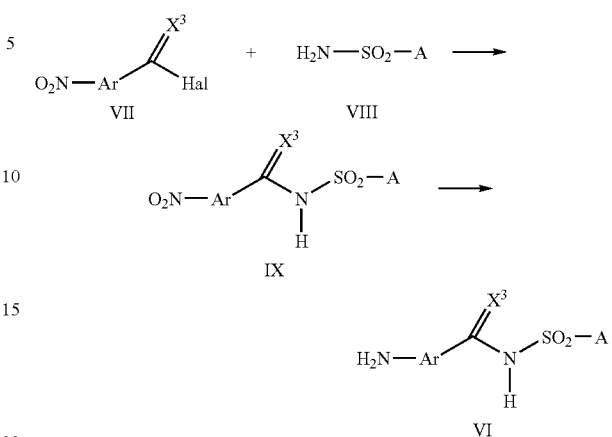

In scheme 1, the variables A, Ar and $X^3$ are each as defined above. The condensation of aroyl compounds of the general formula VII with sulfuric diamides of the general formula VIII to give the corresponding benzoylsulfamides of the general formula IX is based on known processes, for example as described in WO 01/83459, p. 31-35, in PCT/EP 03/05126, whose disclosure content is incorporated by reference.

The reduction of the nitro compound IX to the aniline VI succeeds, for example, with nascent hydrogen. To this end, the nitro compound IX is reacted with an acid in the presence of a base metal. By their nature, base metals are those which are released from a Bronsted acid with evolution of hydrogen. Such metals generally have a standard potential of <0 V and in particular less than or equal to −0.1 V, for example in the range from −0.1 to −1.0 V (in acidic aqueous solution at 15° C. and 1 bar). Examples of suitable metals are Zn, Fe and Sn, in particular Fe. Useful acids for this purpose are either inorganic mineral acids, for example hydrochloric acid or dilute sulfuric acid, or mixtures of inorganic acid and an inert solvent, for example gaseous HCl in an ether or an alcohol or in a mixture thereof, or organic carboxylic acids, appropriately acetic acid, propionic acid or butyric acid.

Useful reducing agents are also metal hydrides and semimetal hydrides such as aluminum hydride and hydrides derived therefrom such as lithium aluminum hydride, diisobutylaluminum hydride, borohydrides such as diborane and borohydrides derived therefrom such as sodium borohydride or lithium borohydride. To this end, the nitro compound IX is contacted in an inert solvent with the complex metal hydride at from 10 to 65° C., advantageously from 20 to 50° C.

A further suitable reducing agent for the conversion of the compound IX to the compound VI is hydrogen in the presence of catalytic amounts of transition metals or transition metal compounds, in particular of the 8th transition group.

The reduction of the compound IX to the compound VI may also be effected with sodium sulfide, advantageously in aqueous ammoniacal solution, in the presence of ammonium chloride in accordance with the process described in Org. Syn., Coll. Vol., 3, 82 (1955).

The aroyl compounds VII used in scheme 1 are obtainable by prior art processes or can be prepared based on known processes, for example in accordance with U.S. Pat. No. 6,251,829, EP 415 641, EP 908 457, EP 1176133 and WO 01/087872.

The process according to the invention enables the preparation of the product of value I in high yields and excellent purity, so that complicated purification processes are not required. The process according to the invention can thus be carried out in a simpler and more economically viable manner than the processes known from the prior art. When the reaction is carried out with an enamine III where $R^{1a}$ is, for example, $C_1$-$C_6$-alkyl, in particular methyl, the compounds described in WO 01/83459 are obtained directly in high yield and purity.

The present invention further provides the reaction of the compounds I where $R^1$=hydrogen obtained by the process according to the invention with
(A) an aminating agent of the formula IV

  IV where $L^1$ is a nucleophilically displaceable leaving group, preferably halogen, hydrogensulfate, $C_1$-$C_6$-alkylsulfonyloxy, $C_1$-$C_6$-haloalkylsulfonyloxy, phenylsulfonyloxy or phenyloxy,
where the phenyl ring is optionally mono- or polysubstituted by halogen, nitro, $C_1$-$C_6$-alkyl or $C_1$-$C_6$-haloalkyl, more preferably halogen, hydrogensulfate, $C_1$-$C_6$-alkylsulfonyloxy, $C_1$-$C_6$-haloalkylsulfonyloxy, phenylsulfonyloxy, p-toluenesulfonyloxy, p-chlorophenylsulfonyloxy, p-bromophenylsulfonyloxy or p-nitrophenylsulfonyloxy, especially preferably chlorine, methylsulfonyloxy, trifluoromethylsulfonyloxy or phenylsulfonyloxy;

to obtain a compound of the formula I where the variables $R^2$, $R^3$, $X^1$, $X^2$, $X^3$, Ar and A are each as defined above and preferably have the preferred definitions and $R^1$ is amino, or with
(B) an alkylating agent of the formula V

  V where
$R^{1b}$ is $C_1$-$C_6$-alkyl, $C_1$-$C_6$-haloalkyl, $C_3$-$C_7$-cycloalkyl, $C_2$-$C_6$-alkenyl, $C_2$-$C_6$-haloalkenyl, $C_3$-$C_6$-alkynyl or $C_3$-$C_6$-haloalkynyl, and preferably $C_1$-$C_6$-alkyl very preferably $C_1$-$C_4$-alkyl; and
$L^2$ is a nucleophilically displaceable leaving group, preferably halogen, hydrogensulfate, $C_1$-$C_6$-alkylsulfonyloxy, $C_1$-$C_6$-haloalkylsulfonyloxy or phenyloxy,
where the phenyl ring is optionally mono- or polysubstituted by halogen, nitro, $C_1$-$C_6$-alkyl or $C_1$-$C_6$-haloalkyl, more preferably halogen, hydrogensulfate, $C_1$-$C_6$-alkylsulfonyloxy, $C_1$-$C_6$-haloalkylsulfonyloxy, phenylsulfonyloxy, p-toluenesulfonyloxy, p-chlorophenyisulfonyloxy, p-bromophenylsulfonyloxy or p-nitrophenylsulfonyloxy, especially preferably chlorine, methylsulfonyloxy, trifluoromethylsulfonyloxy or phenylsulfonyloxy;

to obtain a compound of the general formula I where the variables $R^2$, $R^3$, $X^1$, $X^2$, $X^3$, Ar and A are each as defined above and preferably have the preferred definitions and $R^1$ is as defined for $R^{1b}$.

The process for alkylating or aminating the compound I with $R^1$ is surprising in that the formation of corresponding N-alkylsulfonamides or mixtures of N-alkylsulfonamides or N-alkyl-substituted (thio)uracils or dithiouracils would have been expected. It is known that sulfuric diamides are alkylated in a simple manner with sulfuric diesters or arenesulfonic esters in the presence of a base; see, for example R. Sowada, J. Prakt. Chem. 25, 88 (1964). In the case of trisubstituted sulfuric diamides, the formation of tetrasubstituted sulfuric diamides is known, see B. Unterhalt, E. Seebach, Arch. Pharm. 314, 51 (1981). Sulfuric diamides in which the amide function already bears an acyl radical can also be alkylated, see K. C. C. Bancroft et al., J. Heterocycl. Chem. 15, 1521 (1978); A. Martinez et al., Bioorg. Med. Chem. Lett. 9 (21), 3133 (1999). Those skilled in the art would therefore, as a consequence of the easy alkylatability of the sulfamide side chain, have expected the preferential alkylation on the sulfonamide nitrogen atom or at least the formation of dialkylated products.

The introduction of the amino group on the (thio)uracil ring or dithiouracil ring succeeds surprisingly on the basis of known processes for introducing the amino group on the uracil nitrogen. Such processes are described, for example, in DE 196 52431, whose disclosure content on electrophilic amination is fully incorporated herein by way of reference. Suitable aminating reagents of the formula IV include, for example, 1-aminooxy-2,4-dinitrobenzene or O-mesitylenesulfonylhydroxylamine.

If appropriate, the conversion is effected in the presence of a base. Useful bases are all customary inorganic or organic bases. Suitable bases are, for example, the bases mentioned in connection with the preparation of the compound I by reacting II with III. Preferred bases are alkali metal alkoxides, in particular sodium, lithium, or potassium alkoxides such as sodium methoxide, sodium ethoxide, lithium ethoxide, potassium methoxide, potassium ethoxide, potassium tert-butoxide, sodium tert-butoxide, sodium isopropoxide, potassium tert-pentoxide, alkali metal hydrides such as sodium hydride, potassium hydride, alkali metal carbonates such as lithium carbonate, sodium carbonate, potassium carbonate, cesium carbonate or tertiary amines, in particular amidine bases such as 1,8-diazabicyclo[5.4.0]undec-7-ene. In general, the compound I where $R^1$=hydrogen and the base are used in approximately equimolar amounts.

The reaction of the compound I where $R^1$=hydrogen with an aminating reagent of the formula IV is generally effected in an inert organic solvent or solvent mixture. Solvents preferred for this purpose are nitriles such as acetonitrile, propionitrile or butyronitrile, ketones such as acetone and methyl ethyl ketone, carbonates such as dimethyl carbonate, diethyl carbonate and ethylene carbonate, and also amides such as N,N-dimethylformamide, N,N-dimethylacetamide and N-methylpyrrolidone. Also suitable are organic solvents having basic character, for example the aforementioned tertiary amines such as trialkylamines and pyridine compounds.

In general, the reaction will be carried out at temperatures of from 0 to 80° C., preferably between 10 and 60° C. For this purpose, the compound I where $R^1$=hydrogen and the aminating reagent of the formula IV are generally used in approximately equimolar amounts. However, it is also possible to use one of the components in a greater excess, in which case the excess will preferably not be more than 50 mol %, based on the component present in deficiency.

The workup of the resulting reaction mixture is effected by known methods, for example by aqueous-extractive workup. In this way, phenyl(thio)uracils and phenyl dithiouracils I where $R^1$=NH$_2$ may be prepared in a simple and economically viable way.

In a further variant of the process according to the invention, the enamine of the formula III where $R^{1a}$=hydrogen is initially reacted in the presence of an excess of base with the phenyl iso(thio)cyanate of the formula II without isolating or purifying the compound I where $R^1$=hydrogen. Afterward, the reaction mixture is admixed with an aminating agent of the general formula IV, so that the compound I where $R^1$=amino is obtained directly.

The N-alkylation of the compound I on the free (thio)uracil nitrogen atom succeeds in a manner which is known per se for uracils by reacting compound I where $R^1$=hydrogen with an alkylating agent $R^{1b}$-$L^2$ (V), as described, for example, in U.S. Pat. No. 4,943,309, whose disclosure content on alkylation is fully incorporated by way of reference.

Examples of a suitable, nucleophilically displaceable leaving group $L^2$ are halide, preferably chloride, bromide or iodoide, sulfate, phenylsulfonyloxy where the phenyl radical is optionally mono- or polysubstituted by halogen, nitro or $C_1$-$C_6$-alkyl, such as phenylsulfonyloxy, p-toluenesulfonyloxy, p-chlorophenylsulfonyloxy, p-bromophenyl-sulfonyloxy or p-nitrophenylsulfonyloxy, $C_1$-$C_6$-alkysulfonyloxy such as methylsulfonyloxy, $C_1$-$C_6$-haloalkylsulfonyloxy such as trifluoromethylsulfonyloxy.

$R^{1b}$ is preferably $C_1$-$C_4$-alkyl.

Preferred alkylating, agents are thus $C_1$-$C_4$-alkyl halides, di-$C_1$-$C_4$-alkyl sulfates, $C_1$-$C_4$-alkyl phenylsulfonates where the phenyl radical is optionally mono- or disubstituted by halogen, nitro or $C_1$-$C_6$-alkyl. Particularly preferred alkylating agents are methylating agents or ethylating agents such as dimethyl sulfate, diethyl sulfate, methyl iodide, ethyl iodide, methyl bromide, methyl chloride, ethyl bromide, ethyl chloride, methyl or ethyl $C_1$-$C_6$-alkylsulfonate or the methyl or ethyl esters of the aforementioned phenylsulfonic acids. A very particularly preferred methylating agent is dimethyl sulfate.

In the process according to the invention, the alkylating agent may be used either in an equimolar amount based on the compound I or in a substoichiometric amount or superstoichiometric amount. Typically, at least an equimolar amount of alkylating agent V is used based on the compound I. The molar ratios in which the compound I where $R^1$=hydrogen is used with respect to alkylating agent V are generally in the range from 1:1 to 1:3, preferably from 1:1 to 1:1.3, for the ratio of compound I to alkylating agent V.

Typically, the alkylation is carried out in the presence of a base. Useful bases are in principle all compounds which are capable of deprotonating the lactam nitrogen atom. Suitable bases are, for example, the bases mentioned in connection with the preparation of the compound I by reacting II with III. The base is preferably selected from alkali metal and alkaline earth metal hydroxides such as sodium hydroxide, potassium hydroxide and lithium hydroxide, alkali metal and alkaline earth metal oxides such as calcium oxide, alkali metal and alkaline earth metal carbonates such as lithium carbonate, sodium carbonate, potassium carbonate, cesium carbonate, magnesium carbonate, calcium carbonate, zinc carbonate or barium carbonate. In a particularly preferred embodiment of the process according to the invention, the base used is sodium hydroxide or potassium carbonate.

The base may be used in substoichiometric, superstoichiometric or equimolar amount, based on the compound I. Preference is given to using at least an equimolar amount of base, based on the compound I. The amount of base will generally not be more than 1.3 mol, based on 1 mol of the compound I.

The reaction of the compounds I where $R^1$=hydrogen with the alkylating agent of the formula V is advantageously carried out in the presence of a solvent. Useful solvents for these reactions are, depending on the temperature range, aliphatic, cycloaliphatic or aromatic hydrocarbons such as pentane, hexane, cyclopentane, cyclohexane, toluene, xylene, chlorinated aliphatic and aromatic hydrocarbons such as dichloromethane, trichloromethane, 1,2-dichloroethane, 1,1,2,2-tetrachloroethane, chlorobenzene, 1,2-, 1,3- or 1,4-dichlorobenzene, chlorotoluenes, dichlorotoluenes, open-chain dialkyl ethers such as diethyl ether, di-n-propyl ether, di-n-isopropyl ether, methyl tert-butyl ether, cyclic ethers such as tetrahydrofuran, 1,4-dioxane, anisole, glycol ethers such as dimethyl glycol ether, diethyl glycol ether, diethylene glycol-dimethyl ether, diethylene glycol diethyl ether, $C_1$-$C_4$-alcohols such as methanol, ethanol, n-propanol, isopropanol, n-butanol, ketones such as acetone, methyl ethyl ketone, methyl isopropyl ketone, methyl isobutyl ketone, butanone, carbonates such as diethyl carbonate and ethylene carbonate, N,N-dialkylamides such as N,N-dimethylformamide or N,N-dimethyl-acetamide, N-alkyllactams such as N-methylpyrrolidone, sulfoxides such as dimethyl sulfoxide, tetraalkylureas such as tetramethylurea, tetraethylurea, tetrabutylureas, dimethylethyleneurea, dimethylpropyleneurea or mixtures of these solvents. Preferred solvents are N,N-dimethylformamide, N-methylpyrrolidone, acetone, dichloromethane, tetrahydrofuran, toluene or mixtures of these solvents.

Preference is given to carrying out the alkylation of the compound I at temperatures between −5° C. and 100° C., preferably at temperatures between 0° C. and 80° C. and in particular at temperatures between 20° C. and 50° C. The reaction time may be determined by those skilled in the art in a manner which is customary per se by routine methods such as thin-film chromatography or HPLC.

The compound I, alkylating agent V and base may be added separately, simultaneously or in succession.

Advantageously, the multistage process to prepare the compound I where $R^1$≠hydrogen may also be carried out as a one-pot reaction. The reaction of the phenyl iso(thio)cyanate of the formula II with the enamine of the formula III where $R^{1a}$=hydrogen in the presence of an excess of base results initially in the uracil salt which is subsequently reacted with the alkylating agent without isolation or purification. Afterward, the reaction is conducted to completion within the specified temperature range.

In another variant of the process according to the invention, the reaction may also be carried out in an aqueous multiphasic system, preferably in the presence of phase transfer catalysts such as quaternary ammonium salts or phosphonium salts. Suitable quaternary ammonium salts comprise tetra($C_1$-$C_{18}$)alkylammonium chlorides, bromides, fluorides or tetrafluoroborates such as tetraethylammonium chloride, tetrabutylammonium bromide, tetrabutylammonium iodide, tetrabutylammonium tetrafluoroborate, N-benzyltri($C_1$-$C_{18}$)alkylammonium chlorides, bromides or fluorides such as benzyltriethylammonium chloride, preferably tetrabutylammonium bromide or tetrabutylammonium iodide. Suitable phosphonium salts are, for example, tetraphenylphosphonium chloride or bromide, tetra($C_1$-$C_{18}$)alkylphosphonium chloride or bromide such as tetrabutylphosphonium bromide. In general, the phase transfer catalyst is used in an amount of up to 20 mol %, preferably between 1 and 15 mol % and in particular between 2 and 12 mol %, based on the compound I where $R^1$=hydrogen.

The multiphasic system comprises an aqueous phase and at least one organic liquid phase. In addition, solid phases may also occur in the course of the reaction. The aqueous phase is preferably a solution of alkali metal or alkaline earth metal hydroxides or carbonates in water. With regard to suitable alkali metal or alkaline earth metal hydroxides or carbonates, reference is made to that which was stated before. Particular preference is given to using alkali metal or alkaline earth metal hydroxides, especially sodium hydroxide. For the organic phase, preference is given to aliphatic, cycloaliphatic or aromatic, optionally halogenated hydrocarbons, cyclic or open-chain ethers or mixtures thereof, and reference is made to that which was stated before with regard to the aliphatic, cycloaliphatic or aromatic, optionally halogenated hydrocarbons, cyclic or open-chain ethers. In a preferred embodiment of the process according to the invention, the multiphasic system consists of aqueous sodium hydroxide as the aqueous phase and of toluene and tetrahydrofuran or dichloromethane and tetrahydrofuran as the organic phase.

When a multiphasic system is used, the compound I may, for example, be initially charged in one of the aforementioned organic solvents or solvent mixtures. Afterward, the aqueous solution of the base, the alkylating agent and the phase transfer catalyst are added with mixing and the conversion is then brought to completion within the temperature range mentioned.

The reaction may be carried out continuously or batchwise at atmospheric pressure, reduced pressure or under elevated pressure, if appropriate under inert gas.

The reaction mixture can be worked up to recover the target product I by the methods customary for this purpose. In general, the solvent used will be removed by customary processes, for example by distillation. The target compound I may then be taken up in a water-immiscible organic solvent, any impurities may be extracted with water, acidified if appropriate, and the target compound I may be dried and the solvent removed under reduced pressure. For further purification, the customary processes such as crystallization, precipitation or chromatography may be employed. When a biphasic system is used, workup will generally be effected by extraction.

Compounds of the formula I in which one of the $X^1$, $X^2$ or $X^3$ radicals or each of the $X^1$, $X^2$ and $X^3$ radicals are oxygen may be converted by known methods to compounds of the general formula I where one of the $X^1$, $X^2$ or $X^3$ radicals or each of the $X^1$, $X^2$ and $X^3$ radicals are sulfur by treating with sulfurizing agents. Examples of suitable sulfurizing agents are organophosphorus sulfides such as Lawesson reagent, organotin sulfides or phosphorus(V) sulfides (see also J. March, Advanced Organic Synthesis, 2nd edition, Wiley Interscience 1985, p. 794 and literature cited there). The reaction may be carried out in a solvent or in substance. Suitable solvents are the abovementioned inert solvents and also basic solvents such as pyridine and the like. The temperature required for the reaction is generally above room temperature and is in particular in the range from 50 to 200° C. When the reaction of the enamine III is carried out with an isothiocyanate II in which the $X^1$ radical is sulfur, the corresponding 2-thioxouracils where $X^1$=sulfur are obtained directly.

The process according to the invention affords the uracil compounds of the formula I in good overall yields and with high purity. In addition, it is less complicated than the prior art processes.

The invention is illustrated by the examples which follow.

EXAMPLES

Example 1

Preparation of 2-chloro-5-[3,6-dihydro-2,6-dioxo-4-(trifluoromethyl)-1(2H)-pyrimidinyl]-4-fluoro-N-[[methyl(1-methylethyl)amino]sulfonyl]benzamide Using Sodium Hydride as a Base

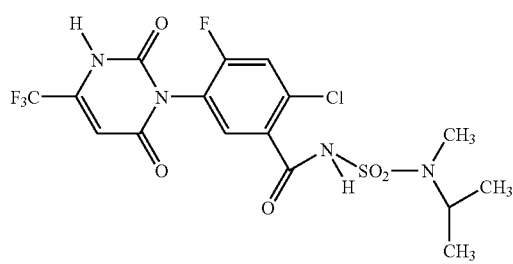

Under nitrogen, a mixture of 1.70 g (9.29 mmol) of ethyl 3-amino-4,4,4-trifluoro-crotonate in 20 ml of N,N-dimethylformamide and 20 ml of n-hexane is stirred under reflux on a water separator for 40 minutes. Afterward, the n-hexane was removed under reduced pressure, the remaining mixture was cooled to from 5 to 8° C. and 0.8 g (20 mmol) of 60% sodium hydride (in mineral oil) was added in 5 portions with stirring. After stirring for a further 15 minutes, a solution of 2.8 g (8.0 mmol) of N-(2-chloro-4-fluoro-5-isocyanatobenzoyl)-N'-methyl-(1-methylethyl)sulfamide in 10 ml of tetrahydrofuran was added with stirring to the yellowish solution and stirring was continued for 2 hours, ultimately at 22° C.

The reaction mixture was admixed with stirring with 2.0 g (33 mmol) of glacial acetic acid and 80 ml of water. After stirring for 40 minutes, crystallization set in. To complete the crystallization, the pH of the aqueous reaction mixture was adjusted to pH 2 using conc. hydrochloric acid and a further 40 ml of water were added. The resulting finely crystalline, slightly yellowish precipitate was filtered off with suction and washed with water and hexane. After drying in methylene chloride over sodium sulfate, the solvent was concentrated to dryness under reduced pressure to obtain 3.9 g (100% of theory) of the title compound having a melting point of 233-236° C. (decomposition).

$^1$H NMR (400 MHz, DMSO-$d_6$)δ (ppm): 12.8 (br, NH), 12.25 (s, NH), 7.82 (d, 1H), 7.76 (d, 1H), 6.4 (s, 1H), 4.1 (m, 1H), 2.8 (s, 3H), 1.12 (d, 3H), 1.12 (d, 6H).

Example 2

Preparation of 2-chloro-5-[3,6-dihydro-2,6-dioxo-4-(trifluoromethyl)-1(2H)-pyrimidinyl]-4-fluoro-N-[[methyl(1-methylethyl)amino]sulfonyl]benzamide Using Potassium Methoxide as a Base In the manner described in example 1, 1.70 g (9.29 mmol) of ethyl 3-amino-4,4,4-trifluorocrotonate in 20 ml of N,N-dimethylformamide were treated with n-hexane. Afterward, the remaining mixture was cooled to −12° C. and 1.47 g (19.9 mmol) of 95% potassium methoxide were added in one portion with stirring. The mixture was stirred at −15° C. for 15 minutes. A solution of 2.8 g (8.0 mmol) of N-(2-chloro-4-fluoro-5-isocyanatobenzoyl)-N'-methyl-(1-methylethyl)sulfamide in 10 ml of tetrahydrofuran was added to the yellowish solution at from −10° C. to −15° C. with stirring within 10 minutes and the mixture was stirred at from −10° C. to −12° C. for 3 hours. The reaction mixture was investigated by thin-film chromatography and it was found that there had been no change in the composition of the reaction mixture during the last 2 hours.

To workup the reaction mixture, it was admixed with 2.0 g (33 mmol) of glacial acetic acid and 120 ml of water, the aqueous reaction mixture was adjusted to pH 2 using conc. hydrochloric acid and the precipitated solid was filtered off with suction. For more rapid drying, the moist precipitate was dissolved in dichloromethane with the addition of 5% by weight of methanol and washed with a saturated sodium chloride solution, and the organic phase was removed. After drying over sodium sulfate and concentrating under reduced pressure, 3.16 g (81% of theory) of the title compound having a melting point of 230-233° C. (decomposition) were obtained. According to HPLC analysis, the compound was 98.2% pure (HPLC column: 250×4 mm, RP 18 LiChrospher, 100 (5 μm) Merck, mobile phase: 60/40% by volume acetonitrile/water over 1 minute, then 80/20% by volume over 7 minutes and finally 60/40% by volume; flow rate: 1 ml/min, UV 254 nm, RT: 1.26 minutes.

Example 3

Preparation of 2-chloro-5-[3,6-dihydro-2,6-dioxo-4-(trifluoromethyl)-1(2H)-pyrimidinyl]-4-fluoro-N-[[methyl(1-methylethyl)amino]sulfonyl]benzamide; Process Using Potassium Carbonate as a Base Under nitrogen, a mixture of 3.3 g (23.8 mmol) of potassium carbonate in 20 ml of N,N-dimethylformamide and 25 ml of n-hexane was heated to reflux at an internal temperature of 70° C. on a water separator with stirring for 30 minutes. The mixture was allowed to cool to 40° C. under nitrogen and then 1.7 g (9.29 mmol) of ethyl 3-amino-4,4,4-trifluorocrotonate were added, the mixture was heated to reflux for a further 30 minutes and then the n-hexane was removed under reduced pressure. With stirring, 2.8 g (8.0 mmol) of N-(2-chloro-4-fluoro-5-isocyanatobenzoyl)-N'-methyl-(1-methyl-ethyl)sulfamide in 10 ml of tetrahydrofuran were added to the resulting slightly reddish mixture which had been cooled to 22° C., and the mixture was stirred at 22° C. for 30 minutes and then at from 50 to 55° C. for 90 minutes. The reaction mixture was investigated by HPLC under the conditions described in example 2 and it was found that the reaction mixture of a sample concentrated under reduced pressure comprised 45% of theory of the title compound having RT=1.26 minutes.

Example 4

Preparation of 2-chloro-5-[3,6-dihydro-3-methyl-2,6-dioxo-4-(trifluoromethyl)-1(2H)-pyrimidinyl]-4-fluoro-N-[[methyl-(1-methylethyl)amino]-sulfonyl]benzamide by reacting N-(2-chloro-4-fluoro-5-isocyanatobenzoyl)-N'-methyl-(1-methylethyl)sulfamide with ethyl 3-methylamino-4,4,4-trifluorocrotonate

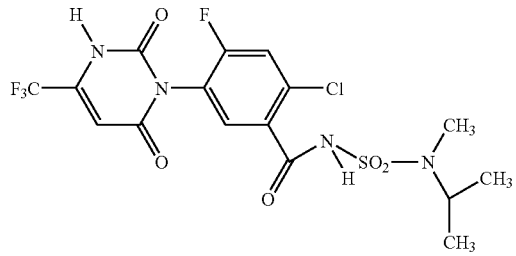

Under nitrogen, 0.99 g (5.021 mmol) of ethyl 3-methylamino-4,4,4-trifluorocrotonate in 25 ml of N,N-dimethylformamide and 50 ml of n-pentane was stirred at reflux on a water separator for 45 minutes. Subsequently, the n-pentane was distilled up to an internal temperature of 70° C. The mixture was allowed to cool to 40° C. and then 1.13 g (10.043 mmol) of potassium tert-butoxide were added in 3 portions with stirring at a temperature of up to 45° C. within 15 minutes to give a red-brown solution. After stirring at 40° C. for 20 minutes, the mixture was allowed to cool and then 1.55 g (4.419 mmol) of N-(2-chloro-4-fluoro-5-isocyanatobenzoyl)-N'-methyl-(1-methylethyl)sulfamide were added at from −15° C. to −10° C. within 2 minutes, resulting in immediate dissolution. The mixture was stirred at −10° C. for 30 minutes, then the reaction mixture was allowed to warm to 22° C. and stirred at this temperature for a further 30 minutes.

With gentle cooling, the resulting reaction mixture was acidified at 20-22° C. with 0.46 g (12.553 mmol) of 4 N hydrochloric acid in 3.1 ml of dioxane and the mixture was concentrated under reduced pressure. The resulting residue was partitioned in a solvent mixture of 100 ml of methyl tert-butyl ether and 100 ml of water. The organic phase was removed, dried over sodium sulfate, filtered through a Alltech ready-to-use column (10 g/60 ml) and then concentrated to dryness under reduced pressure. The resulting residue was stirred at 0° C. in methyl tert-butyl ether for 0.5 h, washed with methyl tert-butyl ether and dried under reduced pressure to obtain 0.97 g (41.6% of theory) of the title compound as a glassy residue having a $^1$H NMR purity of 95%. When the filtrate was concentrated, 0.9 g of a glassy resin was obtained and, according to the $^1$H NMR spectrum, still comprised about 0.45 g (20.3% of theory) of the title compound.

$^1$H NMR (400 MHz, CDCl$_3$)δ (ppm): 9.5 (br, NH), 7.63 (d, 1H), 7.37 (d, 1H), 6.37 (s, 1H), 4.29 (m, 1H), 3.58 (s, 3H), 2.92 (s, 3H), 1.18 (d, 6H).

Example 5

Preparation of 2-chloro-5-[3,6-dihydro-3-methyl-2,6-dioxo-4-(trifluoro-methyl)-1(2H)-pyrimidinyl]-4-fluoro-N-[[methyl-(1-methylethyl)amino]sulfonyl]benzamide by methylating 2-chloro-5-[3,6-dihydro-2,6-dioxo-4-(trifluoromethyl)-1(2H)-pyrimidinyl]-4-fluoro-N-[[methyl(1-methylethyl)amino]sulfonyl]benzamide—without Phase Transfer Catalysis 1.14 g (9.04 mmol) of dimethyl sulfate and 0.283 g (2.055 mmol) of K$_2$CO$_3$ were added to 2.0 g (4.11 mmol) of 2-chloro-5-[3,6-dihydro-2,6-dioxo-4-(trifluoromethyl)-1(2H)-pyrimidinyl]-4-fluoro-N-[[methyl(1-methylethyl)amino]sulfonyl]benzamide from example 1 in 80 ml of N,N-dimethylformamide and the mixture was then stirred at 25° C. for 16 hours. Subsequently, the N,N-dimethylformamide was distilled off at 30° C. and reduced pressure and the residue was taken up in about 250 ml of ethyl acetate. The reaction mixture was acidified with 10% HCl and then extracted twice with water. The organic phase was dried over MgSO4 and the solvent distilled off to obtain 1.95 g of the crude product. According to $^1$H NMR and HPLC, the purity of the product of value was 77% (corresponding to a yield of 73%). For purification, 0.92 g of this crude product was chromatographed on silica gel (28×4.5 cm column) using from 9/1 to 1/1 cyclohexane/ethyl acetate to obtain four fractions. The third fraction (0.58 g; corresponding to 59% isolated yield) comprised the desired product of value in pure form.

$^1$H NMR data (DMSO-d$_6$) δ(ppm): 12.2 (NH), 7.8 (d, 1 H), 7.7 (d, 1 H), 6.6 (s, 1 H), 4.1 (sept, 1 H), 3.5 (s, 3 H), 3.3 (s, 3 H), 2.9 (s, 3 H), 1.2 (d, 6 H)

Example 6

Preparation of 2-chloro-5-[3,6-dihydro-3-methyl-2,6-dioxo-4-(trifluoro-methyl)-1(2H)-pyrimidinyl]-4-fluoro-N-[[methyl-(1-methylethyl)amino]sulfonyl]benzamide by methylating 2-chloro-5-[3,6-dihydro-2,6-dioxo-4-(trifluoromethyl)-1(2H)-pyrimidinyl]-4-fluoro-N-[[methyl(1-methylethyl)amino]sulfonyl]benzamide—with Phase Transfer Catalysis (with Tetrahydrofuran and Toluene as the Organic Phase and Tetrabutylammonium Bromide as the Phase Transfer Catalyst)

12.45 g (0.024 mol) of 2-chloro-5-[3,6-dihydro-2,6-dioxo-4-(trifluoromethyl)-1(2H)-pyrimidinyl]-4-fluoro-N-[[methyl(1-methylethyl)amino]sulfonyl]benzamide (93.9%) from example 1 was added at 25° C. to a solvent mixture of 135 g of toluene and 27 g of tetrahydrofuran, and the mixture was then admixed with a solution of 2.3 g (0.0288 mol) of sodium hydroxide (50%) in 57.5 g of water. 0.77 g (0.0024 mol) of tetrabutylammonium bromide and 3.69 g (0.0293 mol) of dimethyl sulfate were added to the reaction mixture. The biphasic reaction mixture was stirred intensively at 25° C. for 23 hours.

Afterward, the aqueous phase was removed and the organic phase was washed twice with 100 ml of water each time. After drying the combined organic phase, the solvent was distilled off under reduced pressure to obtain 13.8 g of a crude product which, according to quantitative HPLC, comprised 77.5% of the title compound (corresponding to a yield of 88.9%).

Example 7

Preparation of 2-chloro-5-[3,6-dihydro-3-methyl-2, 6-dioxo-4-(trifluoro-methyl)-1(2H)-pyrimidinyl]-4-fluoro-N-[[methyl-(1-methylethyl)amino]sulfonyl] benzamide by methylating 2-chloro-5-[3,6-dihydro-2,6-dioxo-4-(trifluoromethyl)-1(2H )-pyrimidinyl]-4-fluoro-N-[[methyl(1-methylethyl)amino]sulfonyl] benzamide—under Phase Transfer Catalysis (Using Tetrahydrofuran and Methylene Chloride as the Organic Phase and Tetrabutylammonium Iodide as the Phase Transfer Catalyst)

5 g (10.3 mmol) of 2-chloro-5-[3,6-dihydro-2,6-dioxo-4-(trifluoromethyl)-1(2H)-pyrimidinyl]-4-fluoro-N-[[methyl (1-methylethyl)amino]sulfonyl]benzamide from example 1 were added to a solvent mixture of 250 ml of dichloromethane and 125 ml of tetrahydrofuran, and then the mixture was admixed with a solution of 0.411 g (10.3 mmol) of NaOH in 375 ml of water. 0.38 g (1.03 mmol) of tetrabutylammonium iodide and 1.36 g (10.8 mmol) of dimethyl sulfate were added to the reaction mixture and the biphasic mixture was stirred at 1000 revolutions/min for 14 hours.

The aqueous phase was removed and the organic phase was concentrated to dryness under reduced pressure. The chromatographic purification on silica gel was effected in the manner described in example 5 to obtain 4 fractions. After the solvent had been removed, the first fraction comprised 0.54 g of a mixture which, according to $^1$H NMR, consisted of 90% of the desired product of value, and the 2nd fraction 2 comprised 2.4 g of the product of value having a purity of >95% (yield based on both fractions: 56%).

Example 8

2-Chloro-5-[3,6-dihydro-3-methyl-4-(trifluoromethyl)-6-oxo-2-thioxo-1-(2H)-pyrimidinyl]-4-fluoro-N-[[(1-methylethyl)propylamino]sulfonyl]benzamide

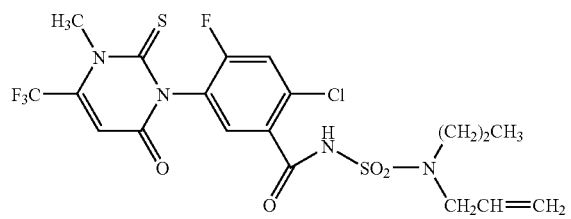

Under nitrogen, a mixture of 30 ml of N,N-dimethylformamide and 50 ml of n-hexane was heated to reflux with stirring for 1 hour and the hexane was subsequently distilled off at an internal temperature of 80-90° C. The mixture was allowed to cool to 30° C. and 0.75 g (3.828 mmol) of ethyl 3-methylamino-4,4,4-trifluorocrotonate was added with stirring, the reaction mixture was cooled to −20° C. and 0.2 g (7.92 mmol) of 95% sodium hydride was added in 3 portions with stirring to form a yellow precipitate. The mixture was stirred at −15° C. for a further 15 minutes and then 1.5 9 (3.828 mmol) of N-(2-chloro-4-fluoro-5-isothiocyanatobenzoyl)-N'-allyl-(1-propyl)sulfamide were added at −15° C. to the mixture. After stirring,for 15 minutes, a brown solution formed. Stirring was then continued at −15° C. for 1 hour and than at 22° C. for 8 hours. The reaction mixture was poured with stirring into 100 ml of 1 N hydrochloric acid and the aqueous mixture was extracted three times with methyl tert-butyl ether. The combined organic phases were reextracted with 1 N hydrochloric acid, then the organic phase was washed with water and the organic phase was dried over magnesium sulfate. After the drying agent had been filtered off, the filtrate was concentrated under reduced pressure. The residue was purified by flash chromatography on silica gel (3×20 cm column, eluent: dichloromethane) and, after the eluate had been concentrated under reduced pressure, 0.65 g (31.3% of theory) of the title compound having a melting point of 74-75° C. was obtained. According to the $^1$H NMR spectrum, a rotamer mixture was present in a ratio of 7:3. According to HPLC analysis, the product peaks for these were at 5.3 and 5.48 minutes having 70 and 25 area percent respectively.

Example 9

2-Chloro-5-[3,6-dihydro-3-methyl-4-(trifluoromethyl)-6-oxo-2-thioxo-1-(2H)-pyrimidinyl]-4-fluoro-N-[[(methylethyl)propargylamino]sulfonyl]benzamide]

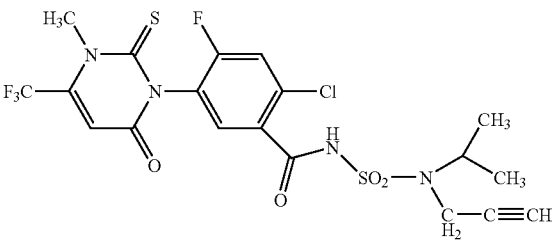

In the manner described in example 8, starting from 1.0 g of N-(2-chloro-4-fluoro-5-isothiocyanatobenzoyl)-N'-propargyl-(1-methylethyl)sulfamide and 0.61 g (3.078 mmol) of ethyl 3-methylamino-4,4,4-trifluorocrotonate, 0.388 g (28% of theory) of the title compound was obtained as a 6:4 rotamer mixture having a melting point of 94-105° C.

We claim:

1. A process for preparing a compound of formula I

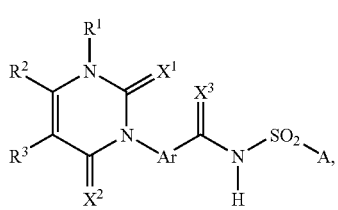

where the variables are each defined as follows:

$R^1$ is hydrogen, cyano, amino, $C_1$-$C_6$-alkyl, $C_1$-$C_3$-cyanoalkyl, $C_1$-$C_6$-haloalkyl, $C_1$-$C_6$-haloalkoxy, $C_3$-$C_7$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl;

$R^2$ and $R^3$ are each independently hydrogen, $C_1$-$C_6$-alkyl, $C_1$-$C_6$-haloalkyl, $C_3$-$C_7$-cycloalkyl, $C_2$-$C_6$-alkenyl, $C_2$-$C_6$-haloalkenyl, $C_3$-$C_6$-alkynyl or $C_3$-$C_6$-haloalkynyl;

$X^1$, $X^2$ and $X^3$ are each independently oxygen or sulfur;

Ar is phenyl, which may be mono- or polysubstituted by the following groups:

hydrogen, halogen, cyano, $C_1$-$C_4$-alkyl or $C_1$-$C_4$-haloalkyl; and

A is —$NR^5R^6$ where the variables $R^5$ and $R^6$ are each independently hydrogen, $C_1$-$C_{10}$-alkyl, $C_2$-$C_{10}$-alkenyl or $C_2$-$C_{10}$-alkynyl, each of which may be unsubstituted or substituted by one of the following radicals:

$C_1$-$C_4$-alkoxy, $C_1$-$C_4$-alkylthio, CN, $NO_2$, formyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl, $C_1$-$C_4$-alkylsulfinyl, $C_1$-$C_4$-alkylsulfonyl, $C_3$-$C_{10}$-cycloalkyl, 3- to 8-membered heterocyclyl having from one to three heteroatoms selected from O, S, N and an $NR^7$ group where $R^7$ is hydrogen, $C_1$-$C_6$-alkyl, $C_3$-$C_6$-alkenyl or $C_3$-$C_6$-alkynyl;

or $C_1$-$C_{10}$-haloalkyl, $C_2$-$C_{10}$-haloalkenyl or $C_2$-$C_{10}$-haloalkynyl;

comprising reacting a phenyl iso(thio)cyanate of the formula II

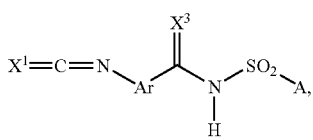

where the variables $X^1$, $X^3$, Ar and A are each as defined above, with an enamine of the general formula III

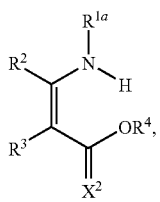

where $R^{1a}$ is as defined above for $R^1$ with the exception of amino;

$R^2$, $R^3$ and $X^2$ are each as defined above; and $R^4$ is $C_1$-$C_6$-alkyl, $C_1$-$C_6$-haloalkyl, $C_1$-$C_3$-alkoxy-$C_1$-$C_3$-alkyl, $C_1$-$C_3$-alkylthio-$C_1$-$C_3$-alkyl, $C_2$-$C_6$-alkenyl, $C_2$-$C_6$-haloalkenyl, $C_3$-$C_6$-alkynyl, $C_3$-$C_6$-haloalkynyl, $C_3$-$C_7$-cycloalkyl, $C_1$-$C_6$-cyanoalkyl or benzyl which is itself unsubstituted or substituted on the phenyl ring by methyl, methoxy, methylthio, halogen, nitro or cyano;

in the presence of from 1.8 to 2.6 base equivalents per mole of the phenyl iso(thio)cyanate of the formula II;

and, if appropriate, in a further step, reacting the resulting 3-phenyl(thio)uracil or 3-phenyldithiouracil of the formula I where $R^1=R^{1a}$, where $R^1$ is hydrogen, with an aminating agent of the formula IV $H_2N$-$L^1$            IV where $L^1$ is a nucleophilic leaving group to give a 3-phenyl(thio)uracil or 3-phenyldithiouracil of the formula I where $R^1$=amino.

2. The process according to claim 1, wherein the reaction is effected in the presence of a base which is selected from alkali metal and alkaline earth metal carbonates, alkali metal and alkaline earth metal alkoxides, alkali metal and alkaline earth metal hydrides and tertiary amines.

3. The process according to claim 1, wherein the reaction is effected in a solvent comprising at least one aprotic polar solvent, and the aprotic polar solvent has a water content of from 0 to 0.5% by weight, based on the total amount of compound II, compound III and solvent.

4. The process according to claim 3, wherein the solvent comprises at least 50% by volume of an aprotic polar solvent selected from carboxamides, carboxylic esters, carbonates, nitriles and sulfoxides.

5. The process according to claim 4, wherein the solvent comprises at least 80% by weight of an aprotic polar solvent.

6. The process according to claim 1, wherein from 0.9 to 1.3 mol of the enamine of the formula III are used per mole of the compound II.

7. The process according to claim 1, wherein a 3-phenyl (thio)uracil or a 3- phenyldithiouracil, where $R^1$ is hydrogen, is prepared and this compound I is subsequently (A) reacted with an aminating agent of the formula IV $H_2N$-$L^1$            IV where $L^1$ is a nucleophilically displaceable leaving group to obtain a compound of the formula I where $R^1$ is amino; and the variables $R^2$, $R^3$, $X^1$, $X^2$, $X^3$, Ar and A are each as defined above; or (B) reacted with an alkylating agent of the formula V $R^{1b}$-$L^2$            V where $R^{1b}$ is $C_1$-$C_6$-alkyl, $C_1$-$C_6$-haloalkyl, $C_3$-$C_7$-cycloalkyl, $C_2$-$C_6$-alkenyl, $C_2$-$C_6$-haloalkenyl, $C_3$-$C_6$-alkynyl or $C_3$-$C_6$-haloalkynyl; and $L^2$ is a nucleophilically displaceable leaving group;

to obtain a compound of the general formula I where $R^1$ is as defined for $R^{1b}$; and the variables $R^2$, $R^3$, $X^1$, $X^2$, $X^3$, Ar and A are each as defined above.

8. The process according to claim 1, wherein the phenyl iso(thio)cyanate of the formula II is described by the formula IIA

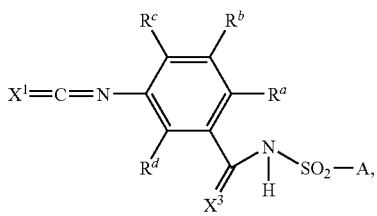

where
$X^1$, $X^3$ and A are each as defined above and
$R^a$, $R^b$, $R^c$ and $R^d$ are each independently hydrogen, halogen, cyano, $C_1$-$C_4$-alkyl or $C_1$-$C_4$-haloalkyl.

9. The process according to claim 8, wherein, in formula IIA,
$R^a$ is halogen, cyano or trifluoromethyl;
$R^c$ is hydrogen or halogen; and
$R^b$ and $R^d$ are each hydrogen.

10. The process according to claim 1, wherein $R^5$ and $R^6$ are each independently
hydrogen, $C_1$-$C_6$-alkyl which optionally carries a substituent selected from the group consisting of halogen, cyano, $C_1$-$C_4$-alkoxy, $C_1$-$C_4$-alkoxycarbonyl, $C_1$-$C_4$-alkylthio, $C_3$-$C_8$-cycloalkyl, furyl, thienyl and 1,3-dioxolanyl which itself optionally carries a substituent selected from the group consisting of halogen and $C_1$-$C_4$-alkoxy;
or
$C_2$-$C_6$-alkenyl or $C_2$-$C_6$-alkynyl which optionally carries 1 or 2 substituents selected from the group consisting of halogen, $C_1$-$C_4$-alkyl, $C_1$-$C_4$-fluoroalkyl, $C_1$-$C_4$-alkoxy, $C_1$-$C_4$-alkoxycarbonyl and nitro.

11. The process according to claim 1, wherein $X^1$, $X^2$ and $X^3$ are each oxygen.

12. The process according to claim 1, wherein $R^1$ is hydrogen, amino or $C_1$-$C_4$-alkyl.

13. The process according to claim 1, herein $R^2$ is hydrogen, $C_1$-$C_4$-alkyl or $C_1$-$C_4$-haloalkyl.

14. The process according to claim 1, wherein $R^3$ is hydrogen.

15. A process of claim 1, wherein $R^1$ is hydrogen, further comprising reacting said compound of Formula I wherein R1 is hydrogen with an alkylating agent of Formula V $$R^{1b}\text{-}L^2 \qquad\qquad V$$

wherein $L^2$ is a nucleophilically displaceable leaving group and
wherein $R^{1b}$ is $C_1$-$C_6$-alkyl, $C_1$-$C_6$-haloalkyl, $C_3$-$C_7$-cycloalkyl, $C_2$-$C_6$-alkenyl, $C_2$-$C_6$-haloalkenyl, $C_3$-$C_6$-alkynyl or $C_3$-$C_6$-haloalkynyl.

* * * * *